(12) United States Patent
Sweeney

(10) Patent No.: US 8,870,836 B2
(45) Date of Patent: *Oct. 28, 2014

(54) METHOD AND DEVICE FOR DELIVERING MEDICINE TO BONE

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 457 days.

This patent is subject to a terminal disclaimer.

(21) Appl. No.: 13/227,230

(22) Filed: Sep. 7, 2011

(65) Prior Publication Data

US 2012/0041395 A1  Feb. 16, 2012

Related U.S. Application Data

(63) Continuation-in-part of application No. 12/822,022, filed on Jun. 23, 2010, now Pat. No. 8,062,270, which (Continued)

(51) Int. Cl.
*A61M 5/32* (2006.01)
*A61B 17/56* (2006.01)

(Continued)

(52) U.S. Cl.
CPC ........... *A61B 17/864* (2013.01); *A61B 17/7258* (2013.01); *A61B 17/7098* (2013.01); *A61F 2002/30677* (2013.01); *A61B 17/8685* (2013.01); *A61B 17/744* (2013.01); *A61B 17/72* (2013.01); *A61B 17/3472* (2013.01); *A61B 2017/00004* (2013.01); *A61B 17/7061* (2013.01); *A61B 10/025* (2013.01)
USPC ............................................. 604/264; 606/60

(58) Field of Classification Search
CPC ................. A61B 17/72; A61B 17/686; A61M 2025/1002; A61M 2025/1015; A61M 2025/105; A61M 2025/1056; A61M 2025/1059; A61M 2025/1081
USPC .......... 604/101.01, 101.03, 101.04, 175, 264; 606/60, 62, 80, 93, 313, 314
See application file for complete search history.

(56) References Cited

U.S. PATENT DOCUMENTS 3,310,051 A  3/1967 Schulte
4,399,814 A  8/1983 Pratt et al.
(Continued)

FOREIGN PATENT DOCUMENTS

WO  WO-02/098307 A1  12/2002
WO  WO-2005/009258 A1  2/2005
WO  WO-2010/019788  2/2010

OTHER PUBLICATIONS

European Search Report for European Patent Application No. 11250603.5-2310, dated Sep. 29, 2011, 6 pages.

(Continued)

*Primary Examiner* — Nathan R Price
(74) *Attorney, Agent, or Firm* — Foley & Lardner LLP

(57) ABSTRACT

A system for communicating fluid to or from a bone includes an insert. The insert includes a shaft extending between proximal and distal ends of the insert, a fenestration, and an expandable portion coupled to the shaft. The shaft is cannulated along at least a portion of the shaft between the proximal and distal ends. The fenestration is disposed along the cannulated portion of the shaft. Outer surfaces of the expandable portion are configured to expand laterally outward to increase the cross-sectional area of the expandable portion orthogonal to the shaft.

19 Claims, 41 Drawing Sheets

Related U.S. Application Data is a continuation-in-part of application No. 12/427,520, filed on Apr. 21, 2009, which is a continuation of application No. 10/704,526, filed on Nov. 7, 2003, now Pat. No. 7,527,611, which is a continuation-in-part of application No. 10/620,287, filed on Jul. 15, 2003, now Pat. No. 7,575,572, and a continuation-in-part of application No. 10/682,307, filed on Oct. 9, 2003, now Pat. No. 7,608,062.

(51) Int. Cl.

| | | |
|---|---|---|
| *A61B 17/86* | (2006.01) | |
| *A61B 17/72* | (2006.01) | |
| *A61B 17/70* | (2006.01) | |
| *A61F 2/30* | (2006.01) | |
| *A61B 17/74* | (2006.01) | |
| *A61B 17/34* | (2006.01) | |
| *A61B 17/00* | (2006.01) | |
| *A61B 10/02* | (2006.01) | |

(56) References Cited

U.S. PATENT DOCUMENTS

| | | | |
|---|---|---|---|
| 4,464,178 A | | 8/1984 | Dalton |
| 4,653,487 A | | 3/1987 | Maale |
| 4,653,489 A | | 3/1987 | Tronzo |
| 4,760,844 A | | 8/1988 | Kyle |
| 4,772,261 A | | 9/1988 | Von Hoff et al. |
| 4,976,692 A | | 12/1990 | Atad |
| 5,047,030 A | | 9/1991 | Draenert |
| 5,203,770 A | | 4/1993 | Wigness et al. |
| 5,380,319 A | * | 1/1995 | Saito et al. ............ 606/28 |
| 5,425,723 A | | 6/1995 | Wang |
| 5,618,286 A | | 4/1997 | Brinker |
| 5,681,289 A | | 10/1997 | Wilcox et al. |
| 5,702,372 A | | 12/1997 | Nelson |
| 5,749,883 A | * | 5/1998 | Halpern ............ 606/159 |
| 5,800,407 A | | 9/1998 | Eldor |
| 5,871,484 A | | 2/1999 | Spievack et al. |
| 6,019,761 A | | 2/2000 | Gustilo |
| 6,048,343 A | | 4/2000 | Mathis et al. |
| 6,077,265 A | | 6/2000 | Werding et al. |
| 6,210,376 B1 | | 4/2001 | Grayson |
| 6,214,012 B1 | | 4/2001 | Karpman et al. |
| 6,220,888 B1 | | 4/2001 | Correa |
| 6,228,088 B1 | | 5/2001 | Miller et al. |
| 6,364,856 B1 | | 4/2002 | Ding et al. |
| 6,387,098 B1 | | 5/2002 | Cole et al. |
| 6,461,327 B1 | * | 10/2002 | Addis et al. ............ 604/101.04 |
| 6,679,890 B2 | | 1/2004 | Margulies et al. |
| 7,527,611 B2 | | 5/2009 | Sweeney |
| 7,575,572 B2 | | 8/2009 | Sweeney |
| 7,608,062 B2 | | 10/2009 | Sweeney |
| 8,062,270 B2 | | 11/2011 | Sweeney |
| 2001/0021852 A1 | | 9/2001 | Chappius |
| 2002/0138146 A1 | | 9/2002 | Jackson |
| 2003/0045885 A1 | | 3/2003 | Margulies et al. |
| 2003/0083662 A1 | | 5/2003 | Middleton |
| 2003/0139751 A1 | * | 7/2003 | Evans et al. ............ 606/127 |
| 2003/0212426 A1 | | 11/2003 | Olson et al. |
| 2004/0225292 A1 | | 11/2004 | Sasso et al. |
| 2005/0015059 A1 | | 1/2005 | Sweeney |
| 2005/0015060 A1 | | 1/2005 | Sweeney |
| 2006/0111767 A1 | | 5/2006 | Olson et al. |
| 2007/0083265 A1 | | 4/2007 | Malone |
| 2009/0204158 A1 | | 8/2009 | Sweeney |
| 2010/0131014 A1 | | 5/2010 | Peyrot et al. |
| 2012/0029432 A1 | | 2/2012 | Sweeney |
| 2012/0041395 A1 | | 2/2012 | Sweeney |

OTHER PUBLICATIONS

Cecil, M.L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878, www.kalindra.com/project.htm, 6 pages.
European Office Action for Application No. 04757057.7, dated Jan. 26, 2010, 5 pages.
European Search Report for European Patent Application No. 04757057.7, mailed Nov. 30, 2009, 3 pages.
Instratek Inc., "Titanium Cannulated Bone Screws Minimize Surgery Time by Eliminating Complicated Procedure Steps," www.instratek.com/bone_screw/, 5 pages.
Press release from Spine Center Atlanta, "New Screw Debut First-time Use for New Spinal Surgery Device," 2002, Orthopaedic & Spine Surgery of Atlanta, LLC. www.SpineCneterAtlanta.com, 2 pages.
Sato, T. et al., "Calcium Phosphate Augmentation of Screw Fixation in Femoral Neck Fracture," 47th Annual Meeting, Orthopaedic Research Society, Feb. 25-28, 2001, San Francisco, CA, 1 page.
SunMedica—Orthopaedic Surgery Products, "orthoPLUG® Hard Bone Design," Redding, CA 96002; www.xunmedica.com, 1 page.
U.S. Appl. No. 12/427,520, filed Apr. 21, 2009, Patrick J. Sweeney.
U.S. Appl. No. 13/227,230, filed Sep. 7, 2011, Patrick J. Sweeney.
U.S. Appl. No. 13/270,072, filed Oct. 10, 2011, Patrick J. Sweeney.
International Search Report and Written Opinion for PCT Application PCT/US2013/052853, dated Jan. 14, 2014, 15 pages.

* cited by examiner

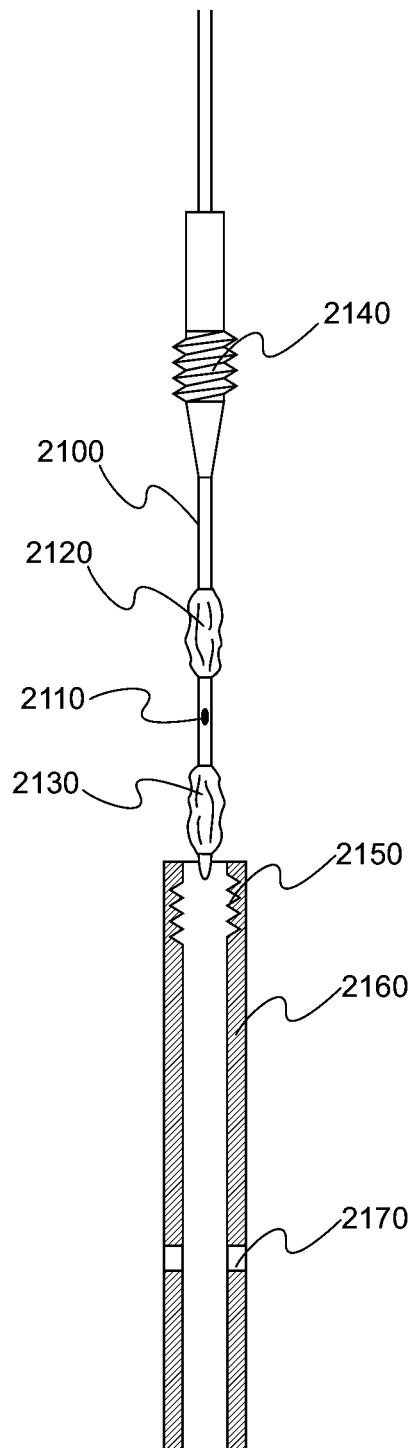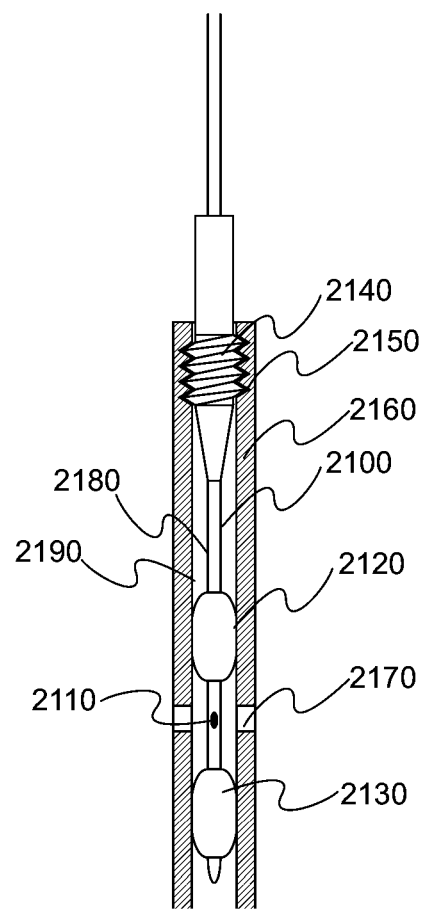
Fig. 21
Fig. 22

METHOD AND DEVICE FOR DELIVERING MEDICINE TO BONE

CROSS-REFERENCE TO RELATED PATENT APPLICATIONS

This is a continuation-in-part of application Ser. No. 12/822,022, filed Jun. 23, 2010, which is a continuation-in-part of application Ser. No. 12/427,520, filed Apr. 21, 2009, which is a continuation of application Ser. No. 10/704,526, filed Nov. 7, 2003, which is a continuation-in-part of application Ser. No. 10/682,307, filed Oct. 9, 2003, and a continuation-in-part of application Ser. No. 10/620,287, filed Jul. 15, 2003. U.S. application Ser. Nos. 12/822,022, 12/427,520, 10/704,526, 10/682,307 and 10/620,287 are all incorporated by reference herein in their entireties.

BACKGROUND

The present invention relates to devices and methods for delivering substances such as medicants to bones and to devices for removing materials from the body. More particularly, the present invention concerns devices and methods for delivering substances to the interior or exterior of fractured or otherwise injured bones, especially to the fracture interface thereof. The present invention also relates to devices and methods for removing materials from the interior or exterior of injured bone. The devices may also be used to promote fusion of a bone or a joint, including a peripheral joint such as a finger or a knee.

Delivery of medicants or therapeutics to bones is an often desirable but difficult-to-achieve process, especially if one desires to focus the delivery to the interior of a bone or to a particular area in a bone. Delivery pins or needles, such as those disclosed in U.S. Pat. No. 6,210,376, the disclosure of which is hereby incorporated by reference herein, are sometimes used to deliver medication or other fluids into bone. Such pins are typically made of metals such as titanium or steel, and must be fabricated ahead of time for later use. Thus, it is difficult to customize the pins for directing the delivery of medicants or fluids to a specific area of interest within a bone. Moreover, such pins do not serve as fixation screws for holding two or more bones or bone pieces in a fixed spatial relationship with respect to each other.

Bone screws can be used to repair or strengthen fractured or otherwise damaged or diseased bones, often by fixing two or more bones or bone pieces with respect to each other, in which case the bone screw may be referred to as a fixation screw. Such screws have been adapted to deliver liquids such as bone cements to the interior of a bone, and are disclosed in U.S. Pat. Nos. 5,047,030 and 6,214,012, for example, the disclosures of which are hereby incorporated by reference herein. These devices must be fabricated ahead of time for later use, thereby substantially limiting the ability to customize the device to the needs of an individual patient. Moreover, while these devices may be suitable for the one-time delivery of a curable substance such as a bone cement, they provide no way to control or regulate the amount of substance delivered. Substance delivery also cannot be directed to certain areas within the bone and not others without changing the location or configuration of the bone screw itself.

Thus, a need exists for a device capable of delivering a substance to a bone, especially to specific areas within the bone, such as a fracture interface. In addition, a further need exists for the ability to customize the delivery location and amount during the course of an operation, once the bone screw is in place, for example.

SUMMARY

In accordance with the present invention, a bone-screw insert is disposed within or along a bone screw to provide a device for the delivery of a desired substance to the interior or exterior of a bone or its surrounding tissues.

In some embodiments, the bone screws and the inserts are cannulated along at least a portion of their lengths. The bone screws are fenestrated and the inserts are either fenestrated or permeable to the substance to be delivered such that when the insert is disposed within the bone screw a delivery pathway exists whereby the substance can be delivered from one end of the insert to the exterior of the bone screw through the bone-screw fenestrations. The bone-screw inserts of the present invention thus allow one to selectively block the bone-screw fenestrations to which substance delivery is not desired, while maintaining a substance delivery pathway to one or more bone-screw fenestrations to which substance delivery is desired.

In other embodiments, inserts, which may be fenestrated or permeable, are disposed along at least a portion of an exterior surface of the bone screws. In these designs, the inserts may be connected to the exterior surface of the bone screws using a variety of attachment means, including but not limited to, grooves, hooks, loops, and the like. For example, the bone screws may have one or more exterior grooves running along at least a portion of their lengths and the inserts may be adapted to fit into the grooves. The inserts may be either fenestrated or permeable to the substance to be delivered such that when the insert is disposed along the exterior surface of the screw a delivery pathway exists whereby the substance can be delivered from one end of the insert to the exterior of the bone screw through permeable insert walls or insert fenestrations.

In one aspect of the present invention the bone screw comprises a fixation screw whereby two or more bones or bone pieces may be held in a fixed spatial relationship with respect to each other. It may often be desirable to deliver a substance at or near the fracture interface of a broken bone, for example. In such a case, the desired positions of bone-screw fenestrations which will align with or match this location may not be known until after the bone screw has been disposed within the bone. The bone-screw inserts of the present invention thus allow one to tailor a substance delivery pathway through one or more insert and/or bone-screw fenestrations after the bone screw has been disposed within a bone.

In another aspect of the invention, the device comprises a reservoir which may serve as a source of the one or more substances to be delivered to the vicinity of a bone. Reservoirs useful in the practice of this invention may comprise the cannulated portions of the bone screw or insert, or they may be reservoirs that are connected to the bone screw or insert for substance delivery. In certain embodiments the present invention may further comprise a pump for facilitating the delivery of the one or more substances to the vicinity of a bone. Such pumps may, for example, aid in the continuous or regulated flow of a fluid into the bone screw or insert for delivery to the desired location.

Yet another aspect of the invention provides methods for administering a substance to a bone. In one embodiment, a method comprises introducing a cannulated, fenestrated bone screw into a bone, introducing a cannulated insert into the bone screw cannulation, and introducing a substance to be delivered into the cannulated portion of the insert. In another embodiment, a method comprises attaching a cannulated insert along at least a portion of an exterior surface of a bone screw, introducing the bone screw into a bone, and introducing a substance to be delivered into the cannulated portion of the insert. The methods may comprise the use of a fenestrated or permeable insert, or the use of reservoirs or pumps to aid in substance delivery. In certain embodiments of the invention the insert may initially serve the purpose of preventing bone fragments, blood, fat, or other materials from entering the cannulated portion of the bone screw, especially during insertion of the bone screw into the bone, for example. This may then be followed by readjustment or realignment of the insert to provide a pathway for the substance to be delivered at a later point in time.

Another embodiment of the invention relates to a device for implantation within a bone. The device includes a first end, a second end and a shaft connecting the first and second ends. The shaft defines a cannulation extending along at least a portion of the length of the shaft. The device also includes a seal coupled to the shaft, the seal having an inner surface facing the cannulation of the shaft. The seal is configured to provide access to the cannulation following implantation of the device within the bone, and the seal is configured to self-seal after access is provided to the cannulation.

Another embodiment of the invention relates to a system for removing a substance from a bone. The system includes an insert having two ends connected by a shaft, and the shaft of the insert is cannulated along at least a portion of its length. The system includes an insert fenestration disposed along the cannulated portion of the insert. The system includes a bone screw having two ends connected by a shaft, and the bone screw is adapted to receive the insert. The system includes a device coupled to the insert and in communication with the cannulated portion of the insert, and the device is configured to draw material from the bone through the insert fenestration into the insert.

Another embodiment of the invention relates to a method for removing a substance from a bone. The method includes introducing a bone screw into the bone. The bone screw has two ends connected by a shaft and a portion adapted to be attached to an insert. The method includes attaching the insert to the bone screw. The insert has two ends connected by a shaft, and the shaft of the insert is cannulated along at least a portion of its length. The insert includes an insert fenestration disposed along the cannulated portion of the insert. The method includes coupling a device to the insert in communication with the cannulated portion of the insert, and removing material from the bone through the insert fenestration via the device.

Another embodiment of the invention relates to a system for communicating fluid to or from a bone. The system includes an insert, which includes a shaft extending between proximal and distal ends of the insert, a fenestration, and an expandable portion coupled to the shaft. The shaft is cannulated along at least a portion of the shaft between the proximal and distal ends. The fenestration is disposed along the cannulated portion of the shaft. Outer surfaces of the expandable portion are configured to expand laterally outward to increase the cross-sectional area of the expandable portion orthogonal to the shaft.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, in which:

FIG. 21 shows an insert having deflated balloons along its length being inserted into a bone screw.

FIG. 22 shows the insert of FIG. 21 with inflated balloons disposed inside the bone screw.

FIG. 26(*b*) shows a perspective view of the insert of FIG. 26(*a*) inserted in a groove running along the length of a fixation nail.

FIG. 29(*b*) shows a schematic cross-sectional view of the bone-screw insert of FIG. 29(*a*) following delivery of a substance to the insert.

FIG. 29(*c*) shows a schematic cross-sectional view of a bone screw with a resealing cap, according to an exemplary embodiment.

FIG. 30(*b*) shows the material removal system of FIG. 30(*a*) with the insert in a second position, according to an exemplary embodiment.

FIG. 33(*b*) shows a schematic cross-sectional view of the insert of FIG. 33(*a*) disposed in a second position within a bone screw, according to an exemplary embodiment.

FIG. 33(*c*) shows a schematic cross-sectional view of the insert of FIG. 33(*a*) disposed in a third position within a bone screw, according to an exemplary embodiment.

DETAILED DESCRIPTION

Figure 1:
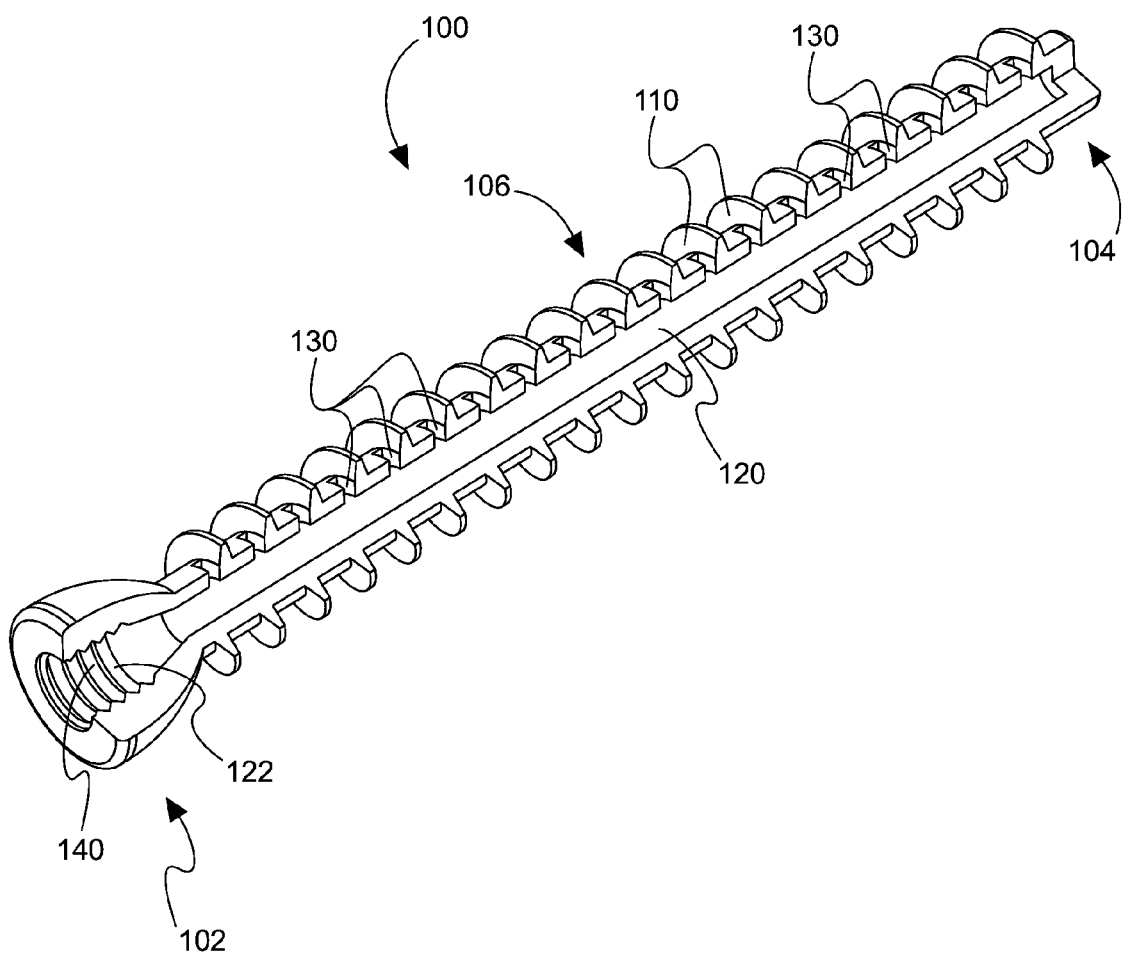
FIG. 1 shows a perspective view of a bone screw in accordance with the present invention.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

In accordance with the present invention, a bone-screw-insert is disposed within a fenestrated bone screw or along an external surface of a bone screw, and the combination is used to deliver desired substances to the vicinity of a bone. The inserts are cannulated along at least a portion of their lengths and the bone screws may have an internal cannulation and/or one or more exterior insert attachment mechanisms running along at least a portion of their lengths. In certain embodiments, the insert may also be fenestrated or permeable to the substance to be delivered. The inserts of the present invention may be comprised of a single piece, or alternatively the insert may be comprised of several pieces or sections. In certain embodiments, the bone screw may be a fixation screw used to hold two or more bones or bone pieces in a fixed spatial relationship with respect to each other. The substances to be delivered may comprise medicants or therapeutics, or other substances which are desirable to deliver to the vicinity of a bone. The substance or a combination of substances may be delivered to the interior of a bone, to the exterior of a bone, to the fracture interface between two or more broken bones, or to any other location which may be facilitated by utilization of the present invention.

For the purposes of this invention, the term "cannulated" means that the screw or insert comprises a hollow cavity disposed inside at least part of its shaft. For example, the cavity may consist of a bore beginning at or near one end of the screw or insert and extending longitudinally into the screw or insert. Other configurations are possible, however, and the hollow cavity need not be restricted to a cylindrical shape or a circular cross-section. The cavity may extend throughout the entire length of the screw or insert, thus creating openings at each end of the screw or insert, or alternatively, the cavity may extend only partially into the interior of the screw or insert. The shape and size of the cavity may be suitably chosen to allow delivery of the desired substance through the screw or insert to the bone area of interest. When it is desired to use the cannulated portion of the screw or insert as reservoir for the substance to be delivered, for example, the cavity may be made as large as possible so long as the screw and insert maintain the structural integrity needed for introduction into the bone.

For the purposes of this invention, the term "fenestration" is used broadly to include any slot, gap, or perforation that defines an opening between the inside of the cannulated portion of the screw or insert to the outside of the screw or insert whereby a desired substance may be delivered. Thus, a fenestrated screw comprises an opening which defines a substance delivery pathway between the internal cannulated portion and the exterior of the screw. Likewise, a fenestrated insert is one that comprises an opening which defines a substance delivery pathway between the internal cannulated portion and the exterior of the insert. In certain embodiments of the present invention where a fenestrated insert is utilized in combination with a fenestrated screw, at least one screw fenestration and at least one insert fenestration may be designed to align with each other once the screw and insert are in their appropriate configuration and position. Alignment or coordination of an insert fenestration and a screw fenestration will define a substance delivery pathway between the internal cannulated portion of the insert and the exterior of the screw.

In accordance with the present invention, fenestrations will typically extend in the radial direction from the internal cannulation to the exterior of the screw or insert, but other configurations are possible. Such fenestrations are separate and distinct from the opening at or near the one end of the screw or insert created by the cannulation. Further in accordance with the present invention, the fenestrations may be any desired shape or size desired to effect the delivery of the desired substance. For example, the fenestration cross-sections may be round, oval, or square. The fenestration cross-sections may, if desired, change shape between the inside and the outside of the screw or insert. Any number or combination of fenestrations may be located along the shaft or at the ends of the screws and inserts of the present invention. The insert fenestrations may be larger or smaller than the screw fenestrations.

An insert may have an outside diameter large enough such that the outside of the insert is pressed snuggly against the inside of the cannulation when the insert is in a bone screw in order to prevent the substance to be delivered from leaking between the insert and the bone screw and escaping through a bone screw fenestration from which it was not intended to escape. Alternatively, the insert may include one or more balloons along its length. These balloons, each of which is disposed around a portion of the insert, may be deflated when the insert is placed into the bone screw and subsequently inflated. Upon inflation, each balloon forms a seal between the outside of the insert and the inside of the bone screw. Using this construction, one or more insert fenestrations and one or more bone screw fenestrations may be isolated between two inflated balloons, such that a substance delivered through the isolated insert fenestrations may exit only through bone screw fenestrations positioned between the inflated balloons. Inserts having different lengths and/or different balloon placements may be provided such that the appropriate insert and bone screw fenestrations may be isolated to provide an appropriate delivery pathway depending on the final position of the bone screw in a patient relative to the desired delivery location.

As an alternative to or in combination with an insert disposed within an internal cannulation in a bone screw, the devices provided herein may include an insert disposed along an exterior surface of a bone screw. Again, the insert may be cannulated and fenestrated or permeable to define a delivery pathway between one end of the cannulation and a portion of a bone. In this embodiment, a bone screw is provided with a means for securing an insert along at least a portion of an exterior surface of the bone screw. For example, the bone screw may include at least one groove, adapted to accept an insert, running along at least a portion of its exterior surface. Alternatively, the bone screw may include one or more attachment mechanisms, such as loops, hooks or the like, along at least a portion of its exterior surface. An insert may be inserted through these loops or hooks, securing the insert to the bone screw. In order to ensure that the attachment elements do not interfere with the insertion of the bone screw into the bone, they are desirably set back from the external circumferential surface of the bone screw. If the bone screw includes threads, the attachment elements desirably do not extend radially beyond the threads. The bone screws may be adapted to secure two or more inserts along their exterior surfaces. This design allows the physician to select the appropriate number and placement for the inserts, depending on the final positioning of the bone screw in a bone.

In some embodiments, a cannulated, fenestrated bone screw may be combined with an exterior insert to provide a delivery pathway between the bone-screw cannulation and the exterior of the bone screw. In this embodiment, an insert is disposed along an external surface of the bone screw and may be used to selectively cover one or more bone-screw fenestrations in order to provide a substance delivery pathway that is appropriate based on the positioning of the bone screw in a bone. For example, a delivery device may include a cannulated bone screw having an exterior groove running along at least a portion of its length and an insert adapted to slide into the groove. Fenestrations are disposed along the groove of the bone screw to allow a substance to pass from the cannulation to the exterior of the bone screw. When a chosen insert is inserted into the groove, it selectively covers those fenestrations that provide a delivery pathway to areas of the bone where delivery of the substance is not needed, while leaving unblocked those fenestrations that provide a delivery pathway to areas of the bone where delivery of the substance is desirable.

For the purposes of this invention, the term "bone screw" is intended to refer to screws of all types which are presently known or hereafter devised for implantation into bone. In this regard, cancellous screws, cortical screws, and machine screws are all contemplated as being within the scope of the types of screws useful in the practice of the present invention. The bone screws of the present invention will typically comprise threads along at least a portion of the exterior of the screw shaft, but it should be appreciated that tacks, pins, nails and the like may also be included within the definition of a bone screw for the purposes of the present invention, whether threaded or unthreaded. When threads are present, it may be found advantageous to use self-tapping threads, or alternatively, the threads can be pre-cut in the bone prior to bone-screw insertion.

Referring now to FIG. 1, there is disclosed a bone screw 100 having two ends 102 and 104 connected by a shaft 106, and bone screw threads 110. The cut-out of FIG. 1 reveals that bone screw 100 comprises a cannulated portion 120, and bone screw fenestrations 130 along the length of the cannulated portion 120. It will be appreciated by one skilled in the art that the fenestrations 130 need not be even spaced along the cannulated portion 120, but may be arranged in a desired pattern or frequency along the length of the cannulated portion 120. It will be further appreciated by one skilled in the art that one end 122 of the cannulated portion 120 of the bone screw 100 is configured to accept a bone screw insert. For example, the bone screw 100 may comprise additional threads 140 on the one end 122 of the cannulated portion 120 to promote fixation of a bone screw insert.

In one embodiment of the current invention the bone screw may be a fixation screw used to hold two or more bones or bone pieces in a fixed spatial relationship with respect to each other. Fixation screws are known in the art. One such device is disclosed by Tronzo, U.S. Pat. No. 4,653,489, the disclosure of which is hereby incorporated by reference herein. In accordance with the present invention, the bone screw may be used to mend peripheral skeletal fractures or osteotomies, repair a spondyloysis or an odontoid fracture, or fuse lumbar facet joints, for example. Other beneficial uses of bone screws, and more particularly, fixation screws, will be known to one skilled in the art and are to be included within the scope of the present invention.

Figure 2:
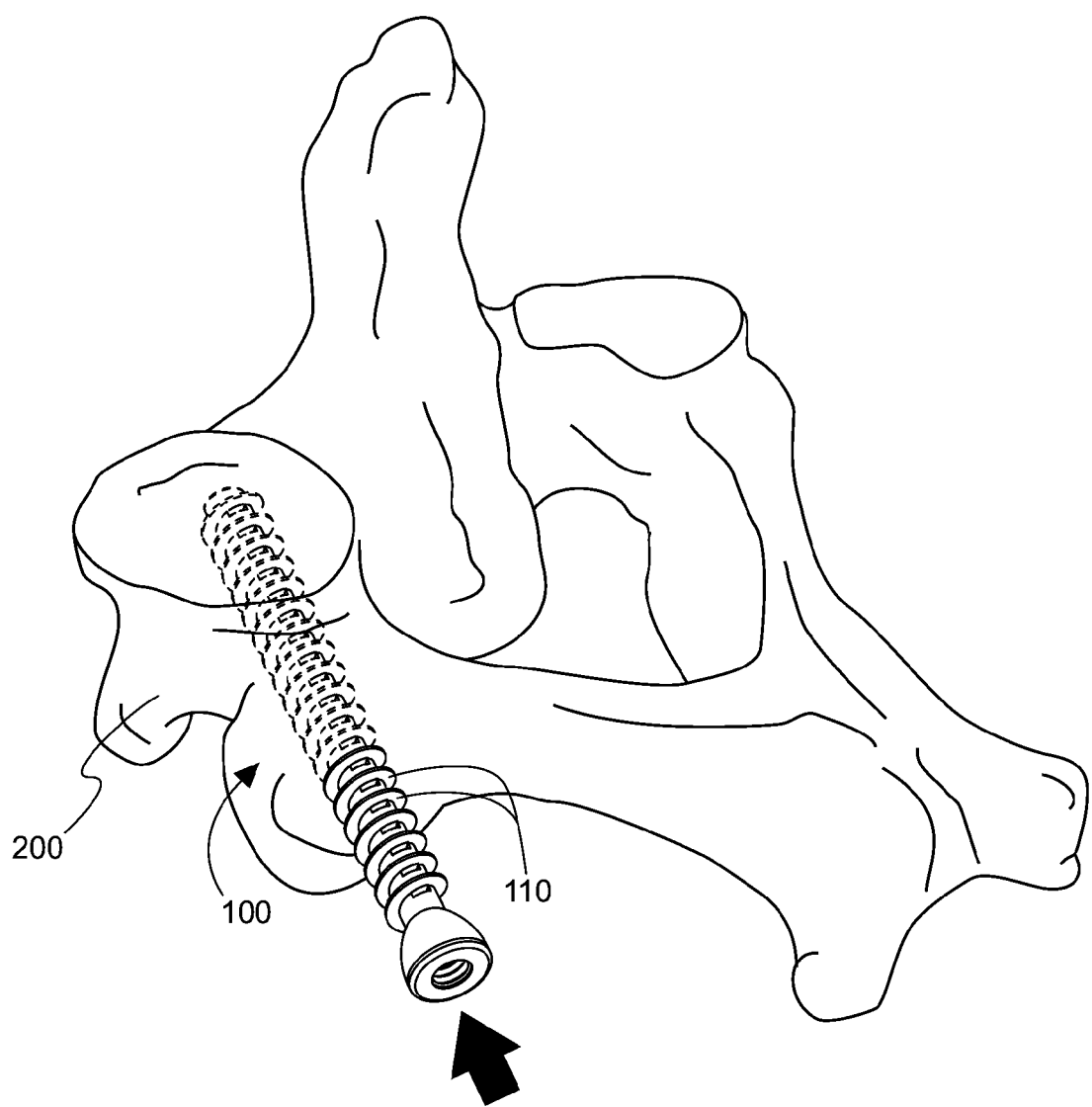
FIG. 2 shows a bone screw inserted into the hip bone of a patient.

Referring now to FIG. 2, there is disclosed a bone screw 100 disposed partially within a bone 200. Bone 200 may, for example, represent a human hip bone. In one embodiment, bone screw 100 is disposed within bone 200 by rotating the bone screw 100 such that the bone screw threads 110 act to pull bone screw 100 into bone 200, thereby anchoring bone screw 100 into place.

Bone screws of the present invention may comprise any material suitable for placement into a bone without harmful effects on the patient. Examples of suitable materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for bone screw construction will be known to those skilled in the art, and are to be included within the scope of the present invention.

Figure 3A:
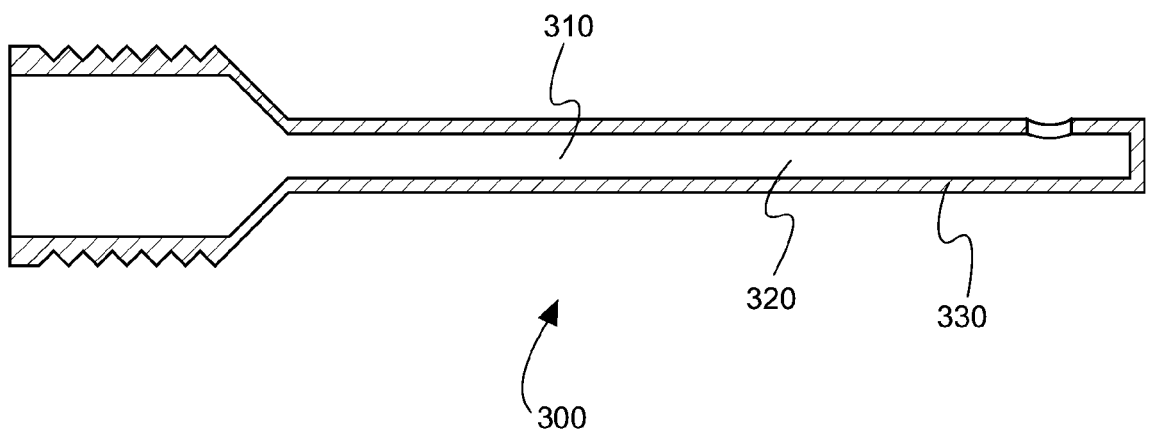
FIG. 3(a) shows a schematic cross-sectional view of a bone-screw insert with a single fenestration.
Figure 3B:
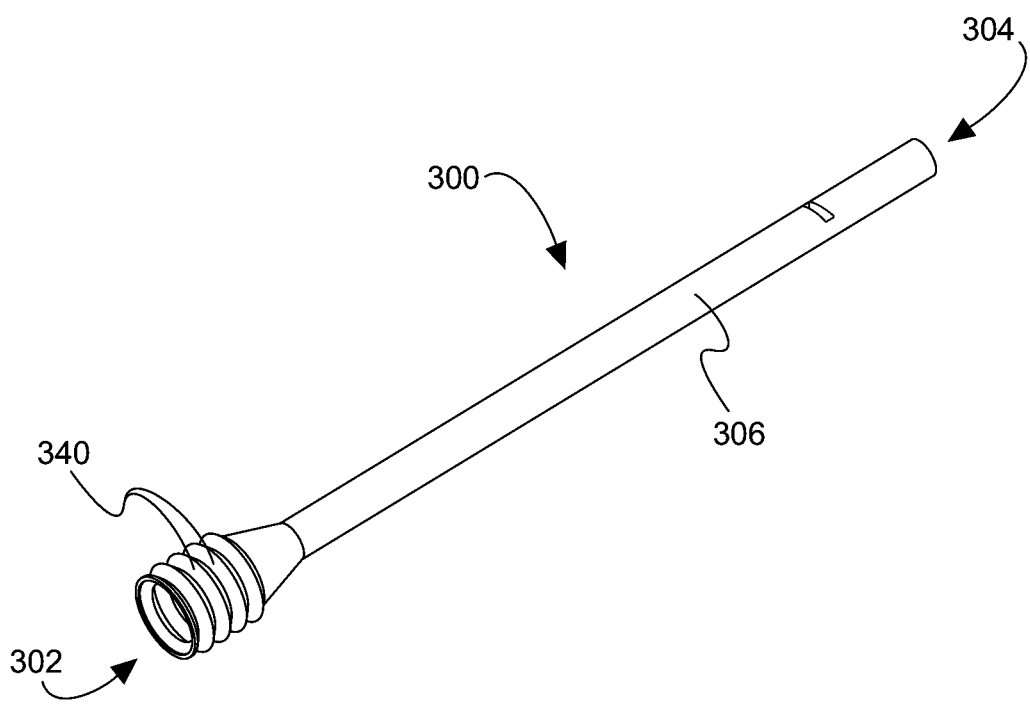
FIG. 3(b) shows a perspective view of the bone-screw insert of FIG. 3(a).

The device of the present invention further comprises a bone-screw insert. For the purposes of this invention, the term "insert" is used to refer to one or more cannulated members which are disposed within the cannulated portion of a bone screw. Referring now to FIG. 3(a), the insert 300 comprises a cannulated portion 310 which consists of a hollow cavity 320 surrounded by the insert wall 330, where the cavity and wall dimensions may be suitably chosen in order to carry out the practice of the invention disclosed herewith. In certain embodiments, the insert may comprise a single piece, as disclosed in FIG. 3(a). Alternatively, the insert may comprise two or more pieces or sections that, when taken together, form the insert of the present invention. Referring now to FIG. 3(b), when the insert 300 is a single piece, the insert comprises two ends, 302 and 304, connected by a shaft 306. The shaft may be cannulated along its entire length, creating openings at each end of the insert. Alternatively, the cannulation may extend only partially into the shaft so long as the cannulation is sufficient to allow for delivery of a substance from one end of the insert to one or more bone-screw fenestrations. One end 302 of the insert 300 may comprise threads 340 which interlock with bone screw threads 140 of FIG. 1 to help fix an insert 300 into a bone screw 100. When the insert comprises two or more pieces or sections, only one of the sections need be cannulated such that the insert sections, when taken together, allow for delivery of a substance from one end of the insert to one or more bone-screw fenestrations.

Figure 4:
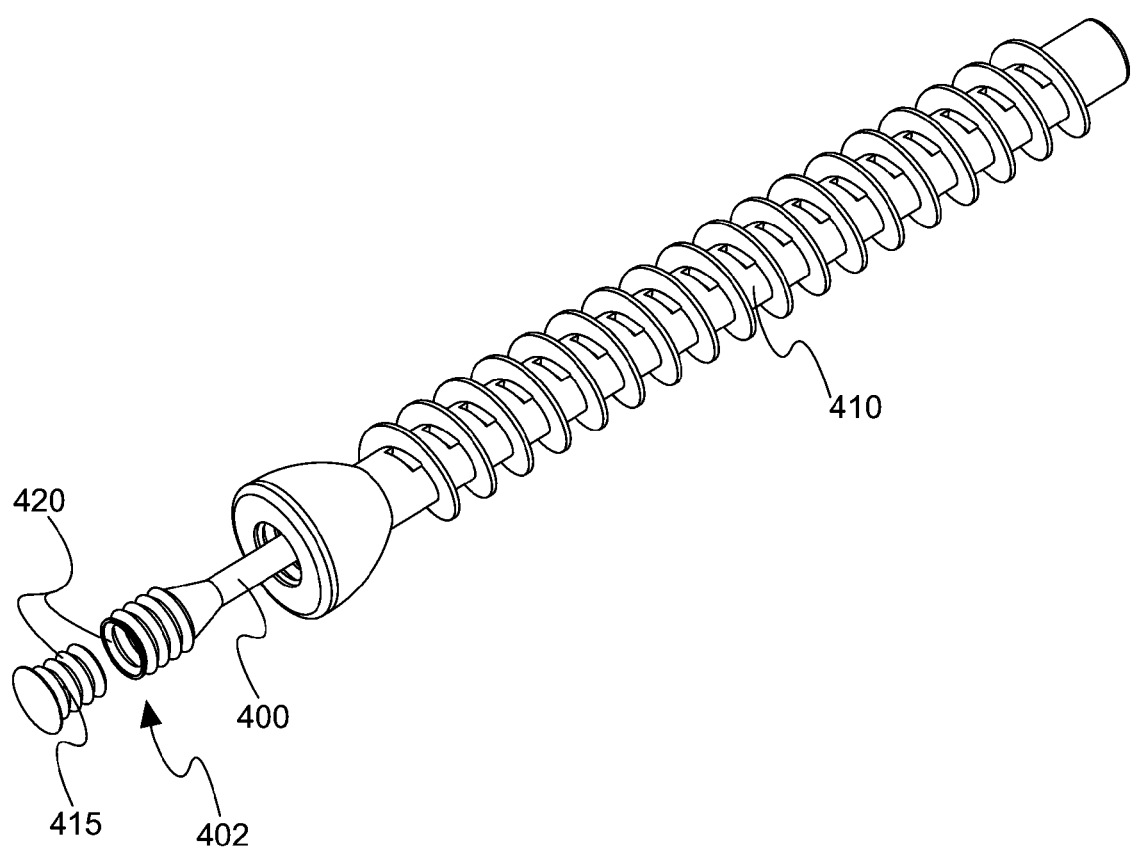
FIG. 4 shows a perspective view of a bone screw, a bone-screw insert, and an insert cap, in accordance with the present invention.

In one embodiment of the present invention, the exterior dimensions of the insert are only slightly smaller than the interior dimensions of a cannulated bone screw to provide for a tight but sliding fit when the insert is placed into the bone screw, as depicted in FIG. 4 in which an insert 400 is shown partially disposed within a bone screw 410. Also disclosed in FIG. 4 is an insert cap 415 which can be used to substantially seal the one end 402 of the insert 400 via insert cap threads 420 either before, during, or after the bone screw 410 and insert 400 are put into place. The insert may have substantially the same cross-sectional shape as the cannulated portion of the bone screw, or their cross-sectional shapes may be different. For example, the internal bone screw cavity and the exterior surface of the insert may have a substantially circular cross-section. One advantage of this embodiment is that after the insert has been disposed within the bone screw, the insert may be rotated with respect to the screw to achieve alignment of certain of the insert and bone-screw fenestrations, for example. In another embodiment, the insert and bone screw may have substantially non-circular cross-sections such that the insert is not free to rotate once it has been disposed within the bone screw. In yet another embodiment, at least part of the insert cross-section may not match that of the bone screw cavity such that when the insert is disposed within the bone screw, one or more channels are formed longitudinally along at least part of the insert and bone screw shafts. Such channels may be useful, for example, to allow air or fluids to escape the bone screw cavity as the insert is introduced.

Figure 5A:
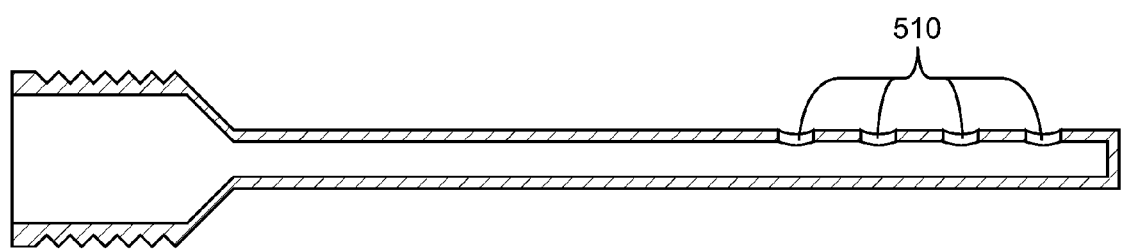
FIG. 5(a) shows a schematic cross-sectional view of a bone-screw insert with multiple fenestrations.
Figure 5B:
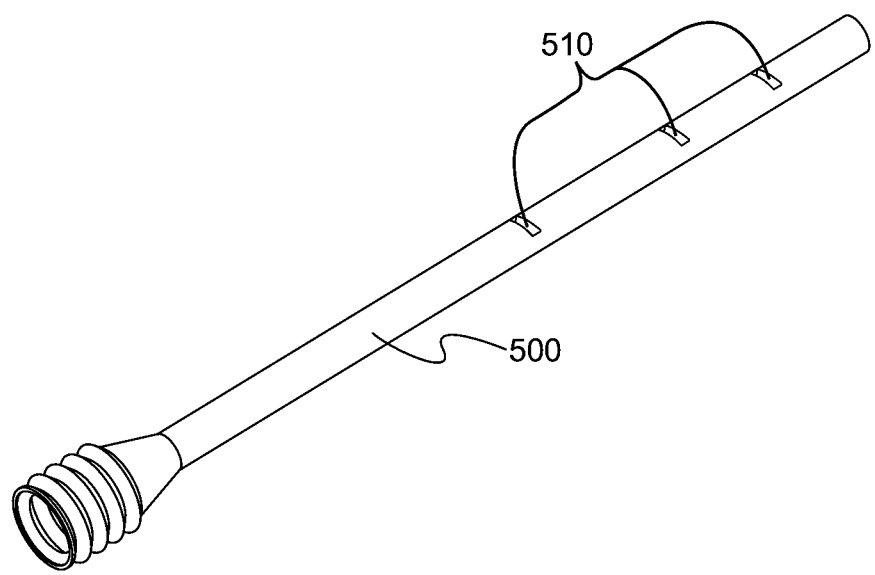
FIG. 5(b) shows a perspective view of the bone-screw insert of FIG. 5(a).

When substantially unimpeded delivery of a substance to one or more bone-screw fenestrations is desired, the inserts of the present invention may comprise one or more insert fenestrations 510, as depicted in FIG. 5(a). An insert having an appropriate number, size, shape, and location of insert fenestrations can be chosen by the practitioner without undue experimentation to provide a delivery pathway between at least one end of the insert and the one or more bone-screw fenestrations. For example, FIG. 5(b) discloses an insert 500 comprising a plurality of insert fenestrations 510 having a substantially rectangular cross-section. Alternatively, the delivery pathway may initiate at one end of the bone screw and pass through the insert to one or more bone-screw fenestrations. The insert fenestrations need not match the bone-screw fenestrations in number, size, shape, or location, although it may be advantageous to locate at least one of the insert fenestrations such that it may be substantially aligned with at least one bone-screw fenestrations once both the bone screw and the insert are in place.

Figure 6:
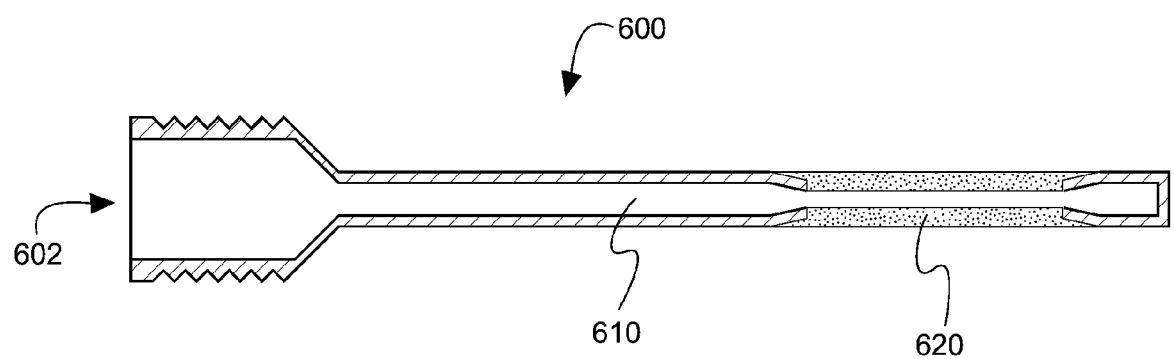
FIG. 6 shows a schematic cross-sectional view of a bone-screw insert with a porous section along the length of the shaft.

In another embodiment of the present invention, the inserts of the present invention may be permeable to the substance to be delivered such that the substance is delivered to the exterior of the insert by diffusion through the insert wall or through small openings in the insert wall. Such openings may be intentionally created such as by increasing the porosity of the insert material (e.g., by introducing a series of pinpricks into the material), or they may exist naturally as pores in the material. Referring to FIG. 6, there is disclosed an insert 600 comprising a cannulated portion 610 and a permeable material 620 wherein a substance to be delivered can travel from one end 602 of the insert to the permeable material 620. When the insert comprises a material that is at least partially permeable to the substance to be delivered, the insert may or may not be fenestrated so long as delivery of the desired substance is not completely impeded by the insert. An embodiment of the present invention comprising a permeable but non-fenestrated insert may be preferred when it is desired to effect a controlled, slow release of the desired substance to a bone, or when it is desired to prevent bone fragments, blood, fat or other materials or fluids from traveling from the exterior of the insert to the interior cavity.

Figure 7:
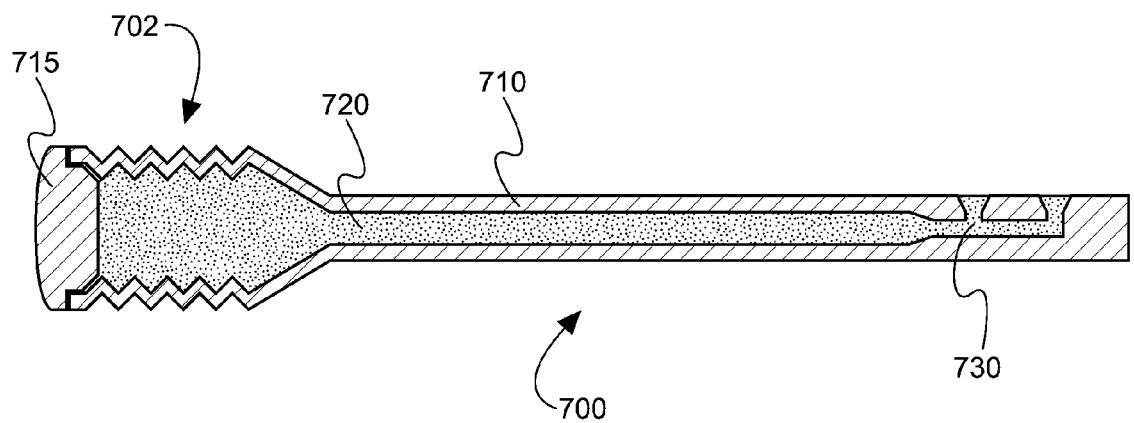
FIG. 7 shows a schematic cross-sectional view of a bone-screw insert with an internal reservoir and a cap.

When it is desired to use the cannulated portion of the insert as a reservoir for the substance to be delivered, or when the substance is to be delivered to a bone by permeation through the insert walls, it may be desirable to make the insert walls as thin as possible. Referring now to FIG. 7, there is disclosed an insert 700 with walls 710 surrounding a reservoir 720. One end 702 of the insert may be substantially sealed by insert cap 715. For example, in one embodiment, the insert may comprise a thin-walled tube which increases the available volume for storage of the substance, and which also increases the diffusion of the substance through the insert wall. In another embodiment, the insert may comprise a film or coating on the interior surfaces of the bone-screw cavity. Inserts in accordance with this embodiment may be as thin as a few hundred nanometers or less, which again may be beneficial for increasing the reservoir size with the bone screw and insert cavity, and for increasing the diffusion of the substance through the insert wall.

In another aspect of the present invention, the delivery of a substance to a bone may alternately be controlled or directed by diminishing the cavity size within the insert so that the movement of the substance is restricted. In this embodiment, it may be desired that the insert cannulation or insert fenestrations be a few microns (e.g., 5 microns) or less in size. Referring again to FIG. 7, there is further disclosed a cannulated portion 730 of insert 700 which is diminished in size so as to restrict or limit the flow of a substance from the reservoir 720. The exact configuration and geometry of an insert providing the desired level of substance delivery can be determined by one skilled in the art without undue experimentation, and all such configurations are to be included within the scope of the present invention.

In yet another aspect of the present invention, the inserts may control or direct the delivery of a substance to a bone through a fenestrated bone screw by substantially blocking one or more of the bone-screw fenestrations. This approach may be advantageous when it is desired to deliver the substance to a specific location with respect to the bone screw's position within the bone. Since the exact bone-screw fenestrations which align with or match this location may not be known until after the bone screw has been disposed within the bone, the bone screw inserts of the present invention allow one to selectively block the bone-screw fenestrations to which substance delivery is not desired, while maintaining a substance delivery pathway to one or more bone-screw fenestrations to which substance delivery is desired. Moreover, by utilizing an insert whereby the insert fenestrations align with the bone-screw fenestrations to which substance delivery is desired, one may achieve substantially unimpeded delivery of the substance to the area of interest.

In addition, the bone-screw inserts of the present invention, even when fenestrated, may be advantageously used to significantly hinder bone fragments, blood, fat, or other materials from entering the cannulated portion of the bone screw, especially during insertion of the bone screw into the bone, for example. In this case it may be desirable to initially position the insert and bone screw such that the insert fenestrations do not align with the bone-screw fenestrations. The insert may then be subsequently re-positioned at a later time to align one or more of the insert fenestrations with the bone-screw fenestrations to facilitate substance delivery.

Inserts of the present invention may comprise any material compatible with the bone screw and able to be placed within the bone screw without producing adverse effects to the patient. Examples of suitable insert materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalcium-phosphate. Other materials useful for insert construction will be known to those skilled in the art, and are to be included within the scope of the present invention. When the insert comprises two or more sections, the sections need not comprise the same material. In addition, when it is desired that the insert be permeable to the substance to be delivered, one or more of the insert sections may comprise a material specifically chosen to impart the desired level of permeability to the insert.

The insert may be sold or otherwise provided in a kit containing two or more inserts having different fenestrations or permeability characteristics. The availability of such a kit has the advantage of allowing a practitioner to select an appropriate insert based on the particular needs of the patient.

In accordance with the present invention, the insert is disposed within the bone screw to provide for a directed or controlled delivery of a desired substance to a bone. For the purposes of this invention, the term "substance" is used to refer to one or more chemical compounds that are useful when delivered to the vicinity of a bone. Substances may be chosen to help treat diseased bone as well as fractured or otherwise injured bones. Alternatively, the substance may be delivered to otherwise healthy bone to help maintain overall bone health, for example. Representative example substances include medicants or therapeutics such as antibiotics, chemotherapeutics, angiogenic factors, bone morphogenic proteins, and bone growth factors. Other desirable substances may be known or hereinafter determined by one skilled in the art, which are to be included within the scope of this invention.

Figure 8A:
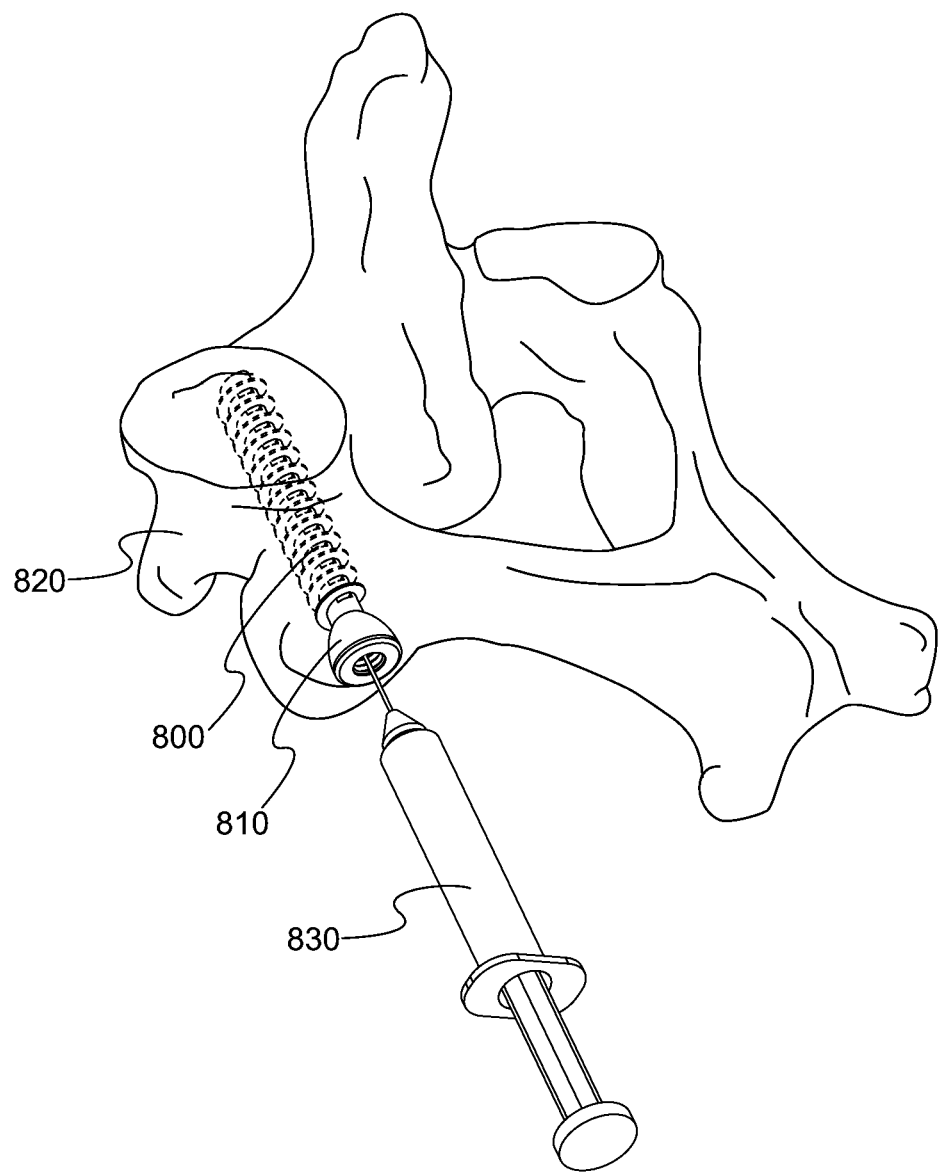
FIG. 8(a) shows a perspective view of a syringe being used to provide a liquid to a bone screw disposed in a hip bone.
Figure 8B:
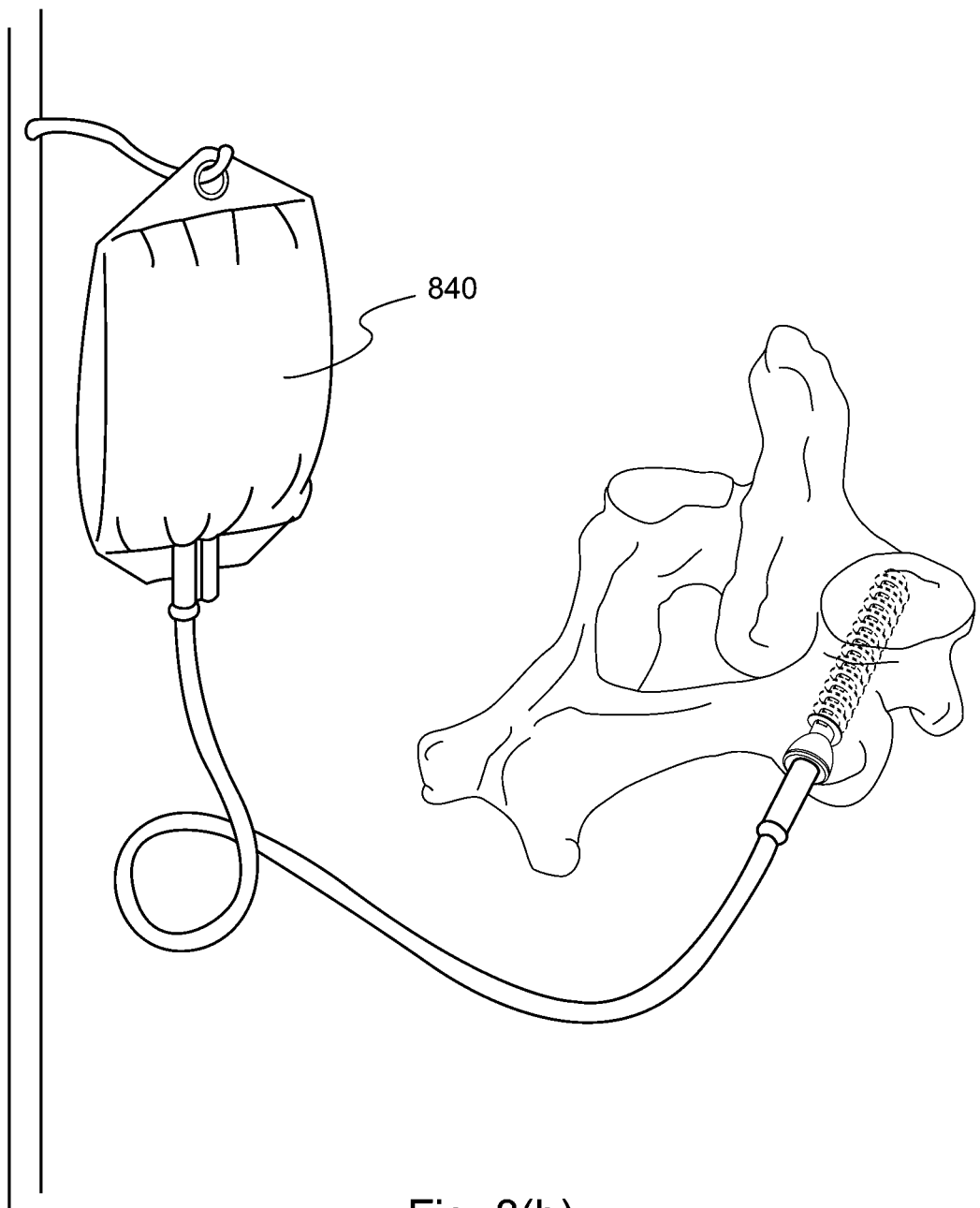
FIG. 8(b) shows a perspective view of a IV being used to provide a liquid to a bone screw disposed in a hip bone.

In certain applications of the present invention it may be desirable that the substance be stored in a reservoir prior to delivery to a bone. Thus, it may be advantageous for the device of the present invention to further comprise a reservoir. For the purposes of this invention, the term "reservoir" refers to any source of the one or more substances to be delivered to the vicinity of a bone. For example, the reservoir may comprise the hollow cavity created by the cannulation of the bone-screw insert and any part of the bone-screw cannulation not occupied by the insert, as depicted in FIG. 7 and described above. In one embodiment of the present invention, the substance to be delivered may be absorbed into a sponge-like material such as a collagen, for example, which may then be disposed within the cannulated portion of the bone screw or insert, or both. When additional reservoir space is desired, a suitable reservoir may be connected to the cannula opening of either the bone screw or insert. For example, FIG. 8(a) discloses a bone screw 800 and an insert 810 disposed therein, both of which are disposed within a bone 820. FIG. 8(a) further discloses a syringe 830 which acts as a reservoir in accordance with the present invention to provide a substance to the bone 820 via bone screw 800 and insert 810. Another embodiment of the present invention, is depicted in FIG. 8(b) which discloses an IV 840 which serves as a reservoir for delivering a substance to a bone via a bone screw and an insert. In yet another embodiment of the present invention, the reservoir may be implanted beneath the patient's skin, i.e., subcutaneously.

Figure 9:
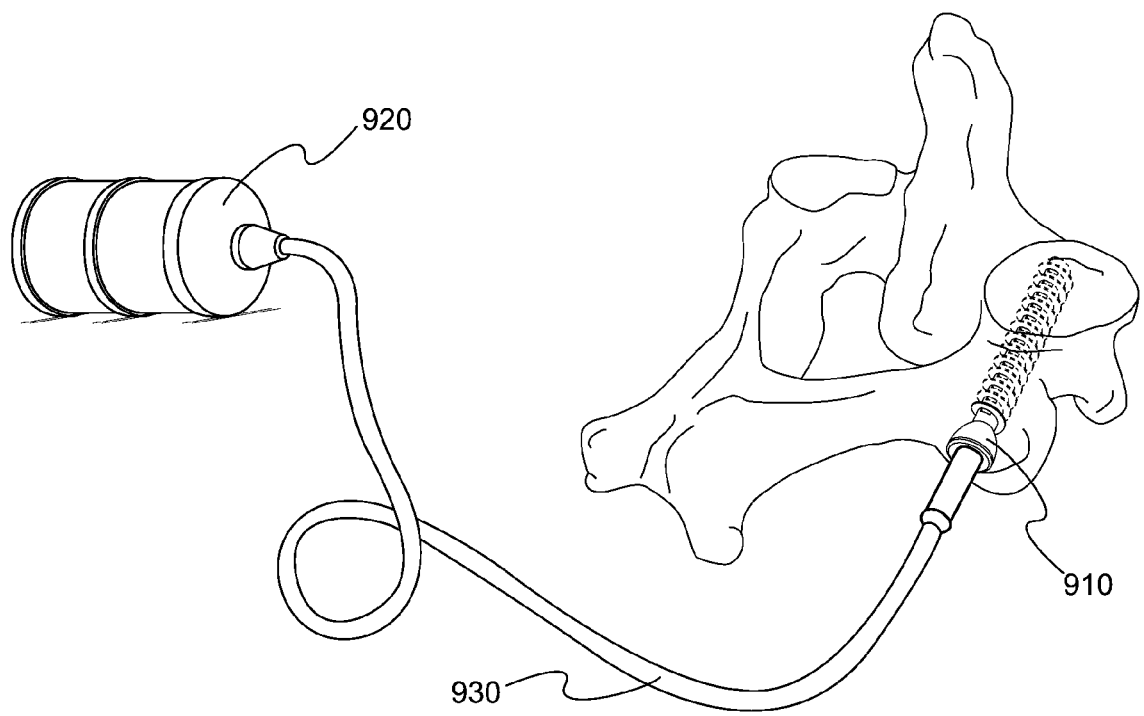
FIG. 9 shows a perspective view of a pump assembly being used to provide a liquid to a bone screw disposed in a hip bone.

In another aspect of the present invention, it may be advantageous for the device of the present invention to further include a pump 920, as depicted in FIG. 9, for delivering a substance to a bone via a bone screw and an insert 910, and tubing 930. A pump may be utilized to aid in delivery of the substance to the vicinity of a bone by, for example, delivering a continuous, regulated volume to the screw. The pump may also be used to increase the fluid pressure within the cannulated portion of the insert, thereby aiding fluid flow through the insert fenestrations or insert walls, for example. This embodiment may have the further advantage that the positive pressure created by the pump within the cannulated portion of the insert or bone screw hampers the influx of unwanted materials or compounds into the device. The pump may be connected to the cannulated portion of the bone screw or insert as depicted in FIG. 9, and the pump may also be implanted subcutaneously if desired. Examples of pumps which may be suitably used in the practice of the current invention are the implantable pumps disclosed in U.S. Pat. No. 4,588,394, for example. Other examples may be relatively simple pumps such as external pumps similar to those used with patient controlled anesthesia machines or simple IV pumps. These and other pump types and designs which may be currently known or hereinafter discerned by one skilled in the art are to be included within the scope of this invention.

In one embodiment of the invention the bone screw may be a fixation nail that holds two or more bones or bone parts in a fixed spatial relationship. In this embodiment the exterior of the bone screw shaft is unthreaded. In accordance with the invention, the fixation nail may be adapted for use in the fixation of a variety of bones, including, but not limited to, femur fixations, humerus fixations and tibia fixations.

Figure 10:
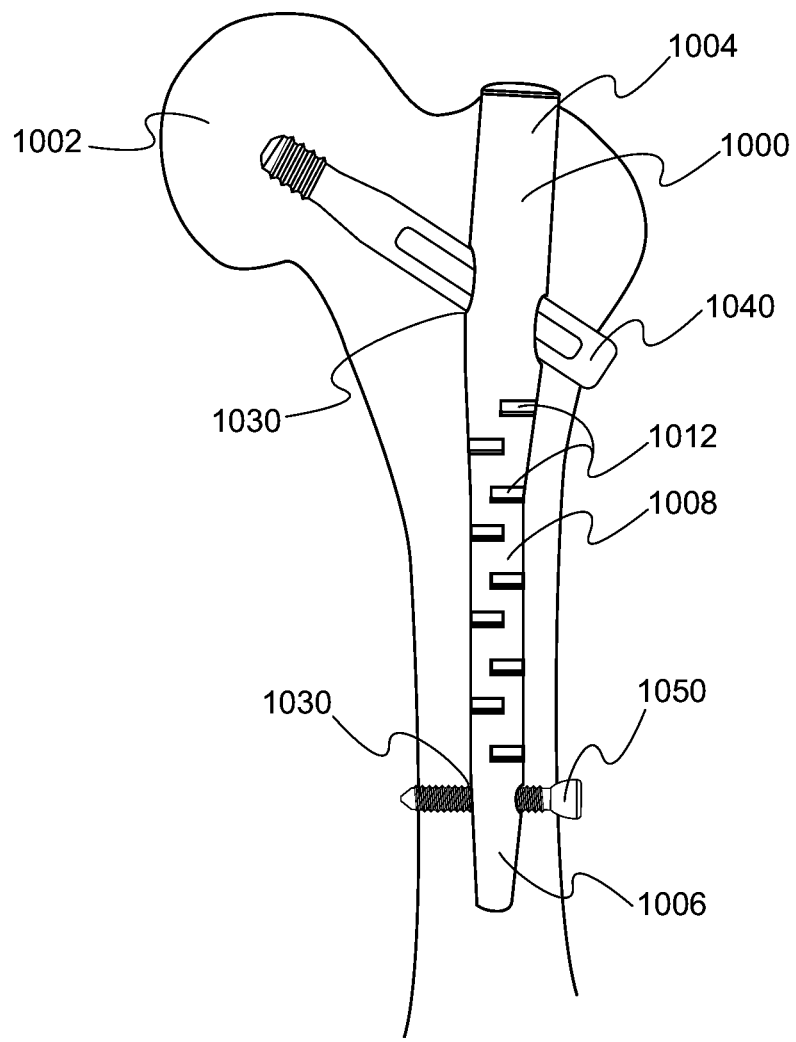
FIG. 10 shows a fixation nail inserted into the femur bone of a patient.
Figure 11:
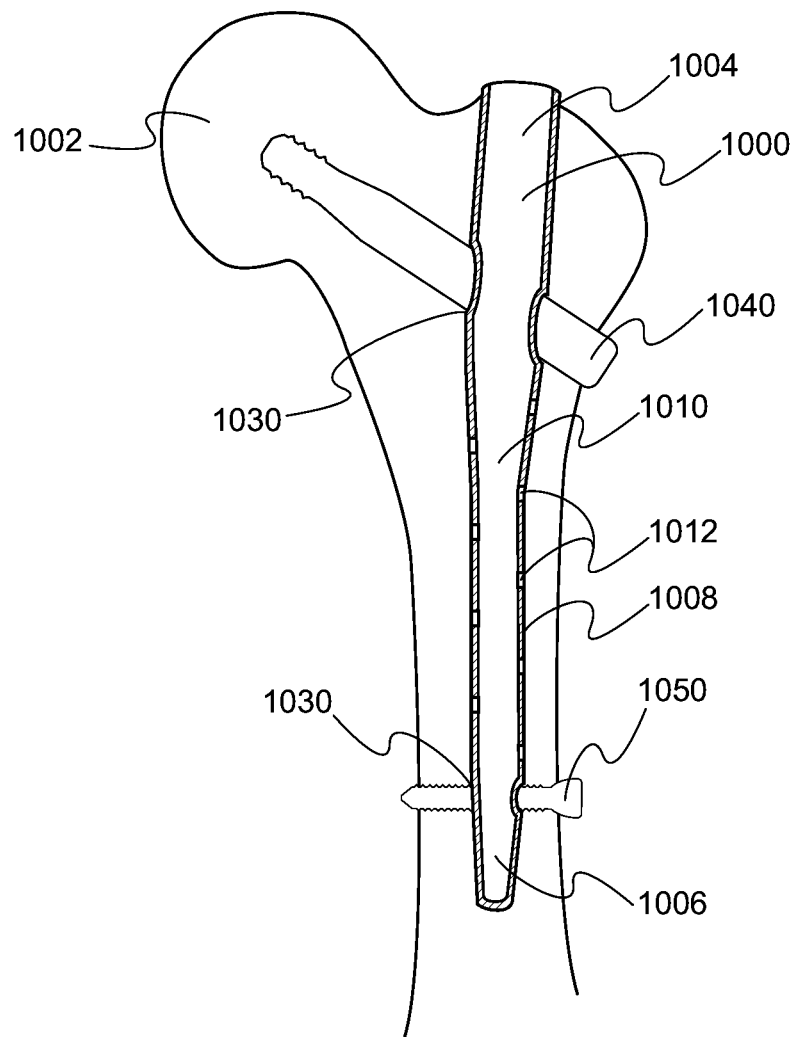
FIG. 11 shows a cross-sectional view of the fixation nail of FIG. 10.
Figure 12:
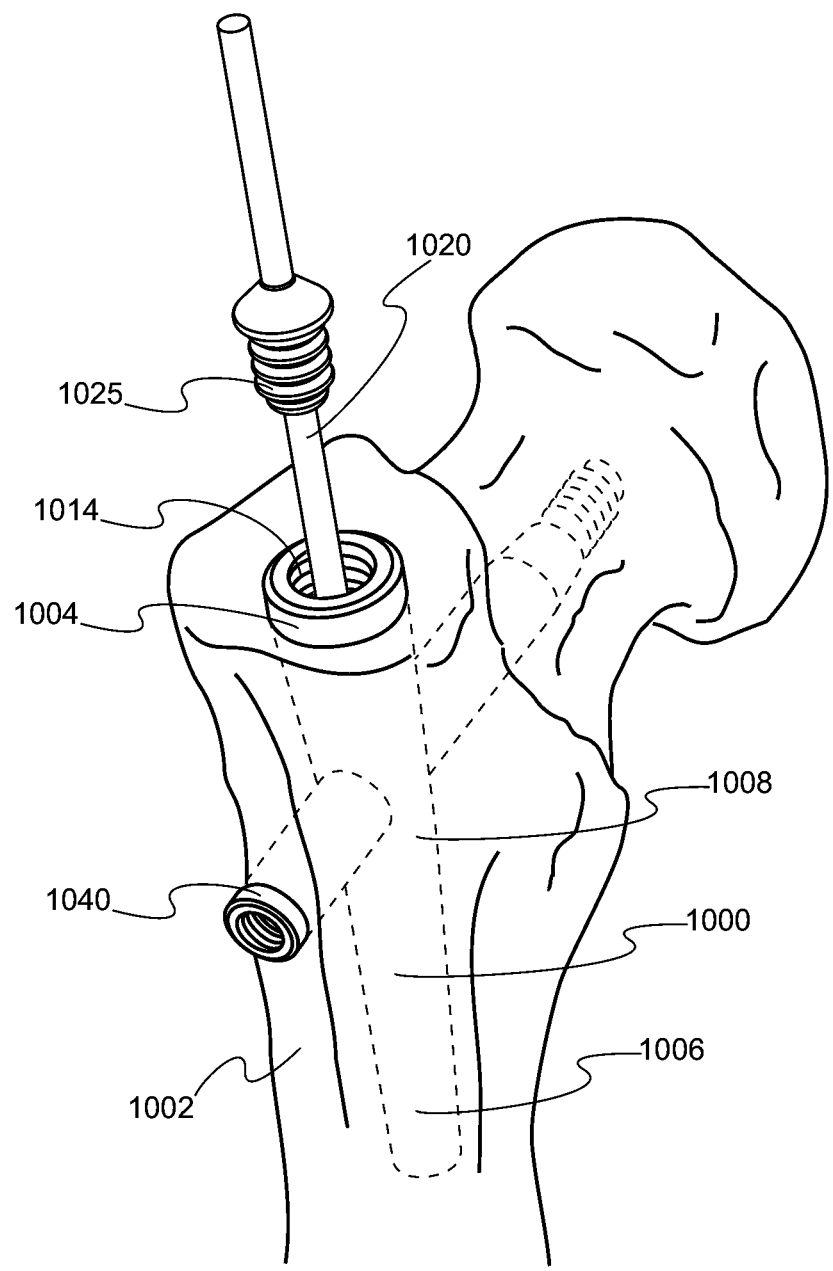
FIG. 12 shows a perspective view of a bone-screw insert being inserted into the fixation nail of FIG. 10.

Referring now to FIG. 10, there is disclosed a femur fixation nail 1000 disposed within a femur 1002. The fixation nail has two ends 1004 and 1006 connected by a shaft 1008. The fixation nail includes a cannulated portion 1010, which is best seen in the cross-sectional view of FIG. 11, and fixation nail fenestrations 1012 along the length of the cannulated portion 1010. One end of the cannulated portion 1010 of the fixation nail 1000 may be configured to accept a nail insert 1020. This is demonstrated in FIG. 12 which shows a perspective view of the fixation nail 1000 having internal threads 1014 on one end 1004 of the cannulated portion 1010 to promote fixation of a nail insert 1020 having threads 1025 on one end. As shown in the figures, the fixation nail may define one or more bores 1030 through its length through which fixation screws 1040 and 1050 may be passed in order to affix the fixation nail to the bone. The fixation screws may pass through the fixation nail substantially perpendicular to the long axis of the nail or they may pass through the nail at acute or obtuse angles with respect to the long axis of the nail. The dimensions of a fixation screw that passes through the cannulated portion of a fixation nail are desirably selected such that the screw does not substantially impede the passage of a substance to be delivered to the bone. In some instances, the fixation screw may itself include a bore through its length that allows for the passage of the substance.

Figure 13:
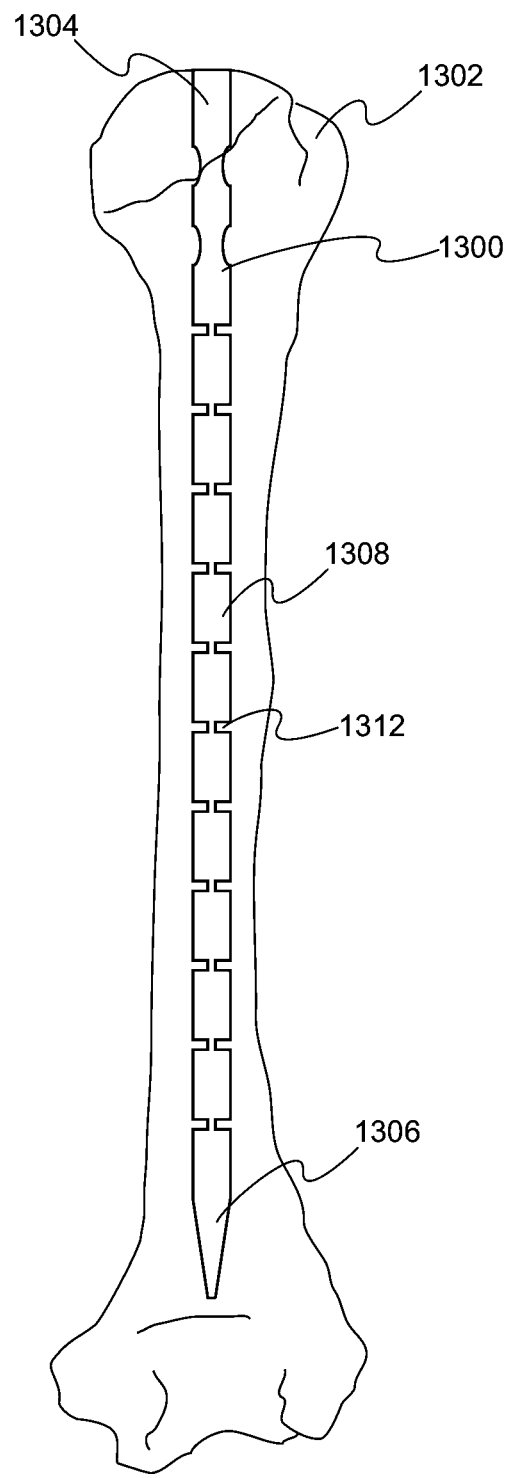
FIG. 13 shows a fixation nail inserted into the humerus bone of a patient.
Figure 14:
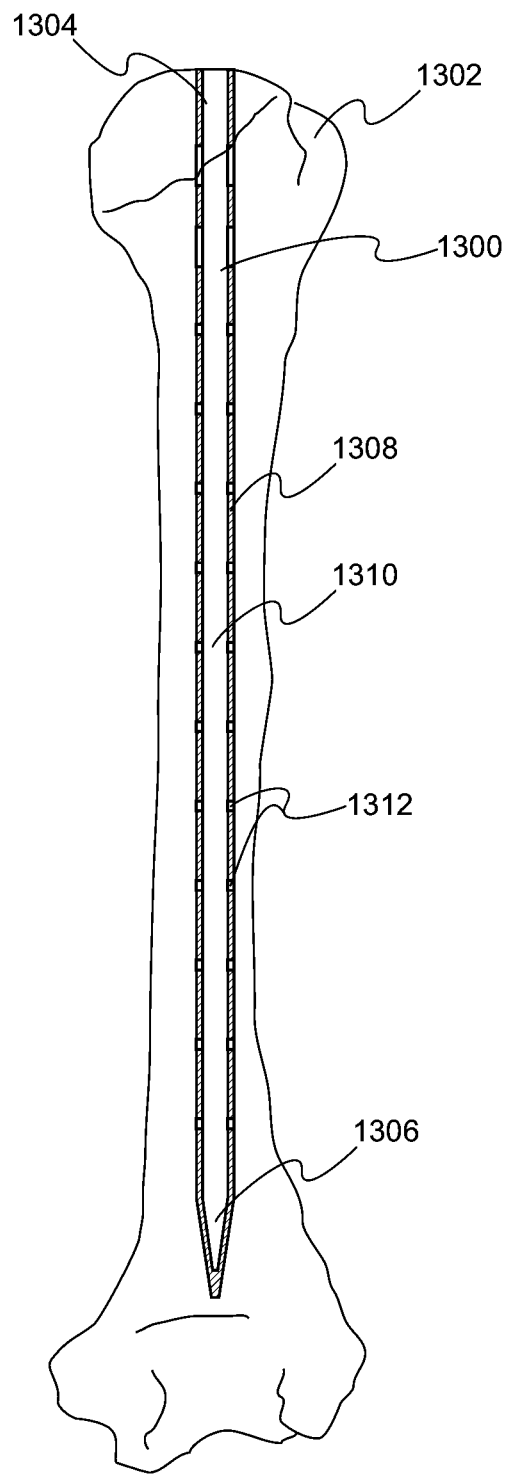
FIG. 14 shows a cross-sectional view of the fixation nail of FIG. 13.
Figure 15:
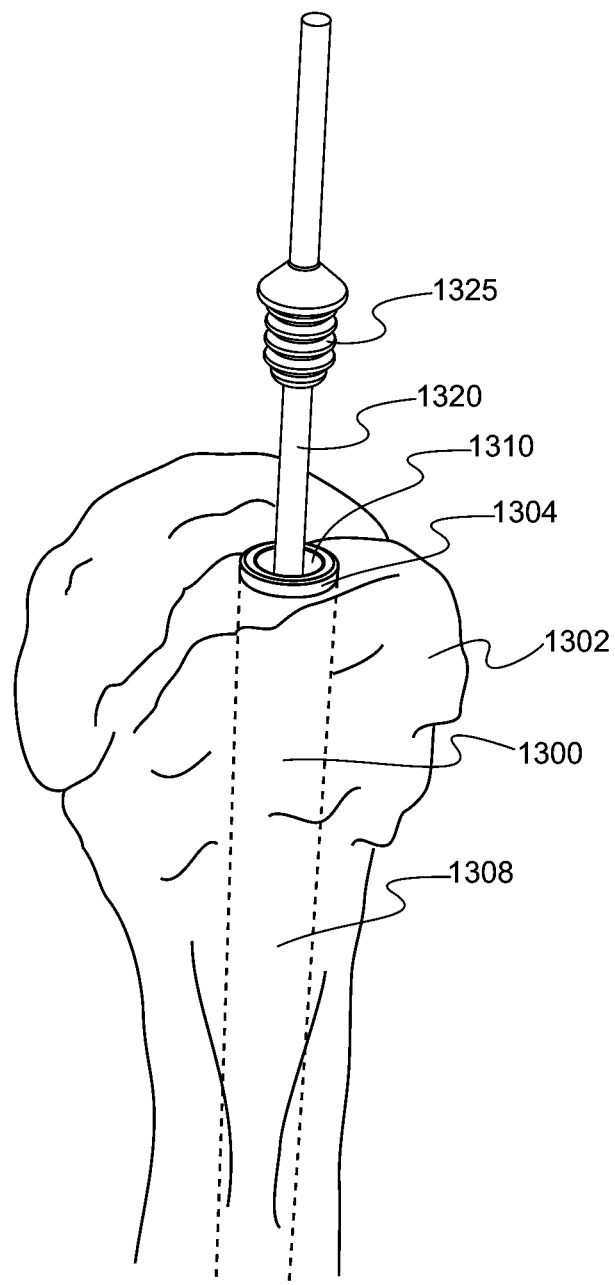
FIG. 15 shows a perspective view of a bone-screw insert being inserted into the fixation nail of FIG. 13.

Referring now to FIG. 13, there is disclosed a humerus fixation nail 1300 disposed within a humerus 1302. The fixation nail has two ends 1304 and 1306 connected by a shaft 1308. The fixation nail includes a cannulated portion 1310, which is best seen in the cross-sectional view of FIG. 14, and fixation nail fenestrations 1312 along the length of the cannulated portion 1310. One end of the cannulated portion 1310 of the fixation nail 1300 may be configured to accept a nail insert 1320. This is demonstrated in FIG. 15 which shows a perspective view of a nail insert 1320 being inserted into the cannulated portion 1310 of the fixation nail 1300. The fixation nail 1300 has internal threads (not shown) on one end of its cannulated portion 1310 to promote fixation of the nail insert 1320 which also has threads 1325 on one end.

Figure 16:
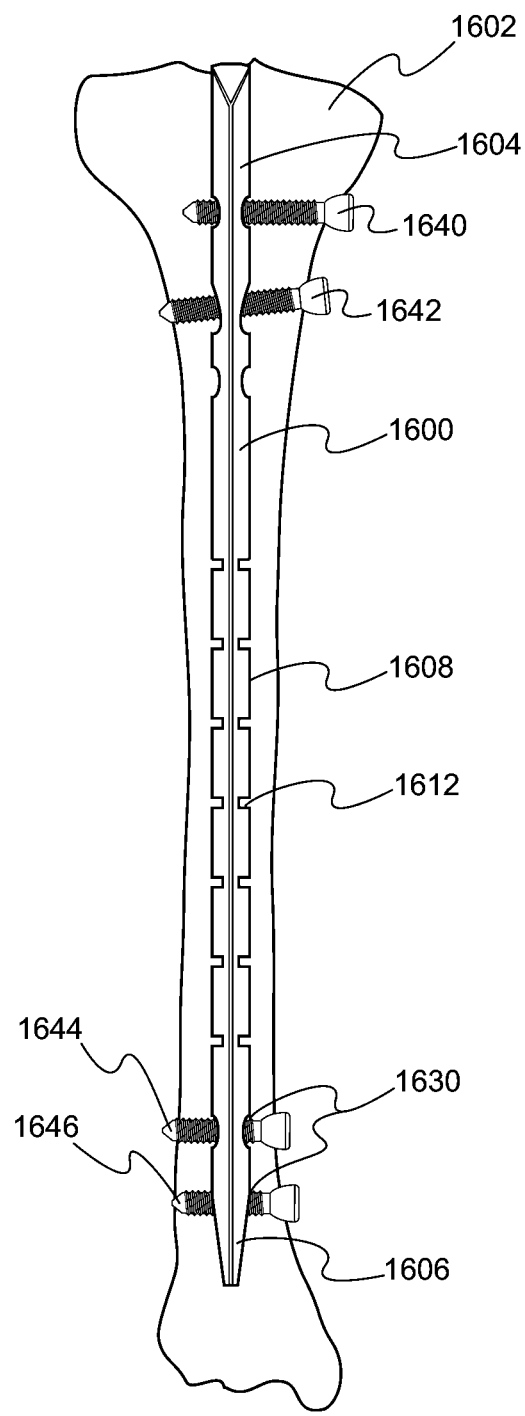
FIG. 16 shows a fixation nail inserted into the tibia bone of a patient.
Figure 17:
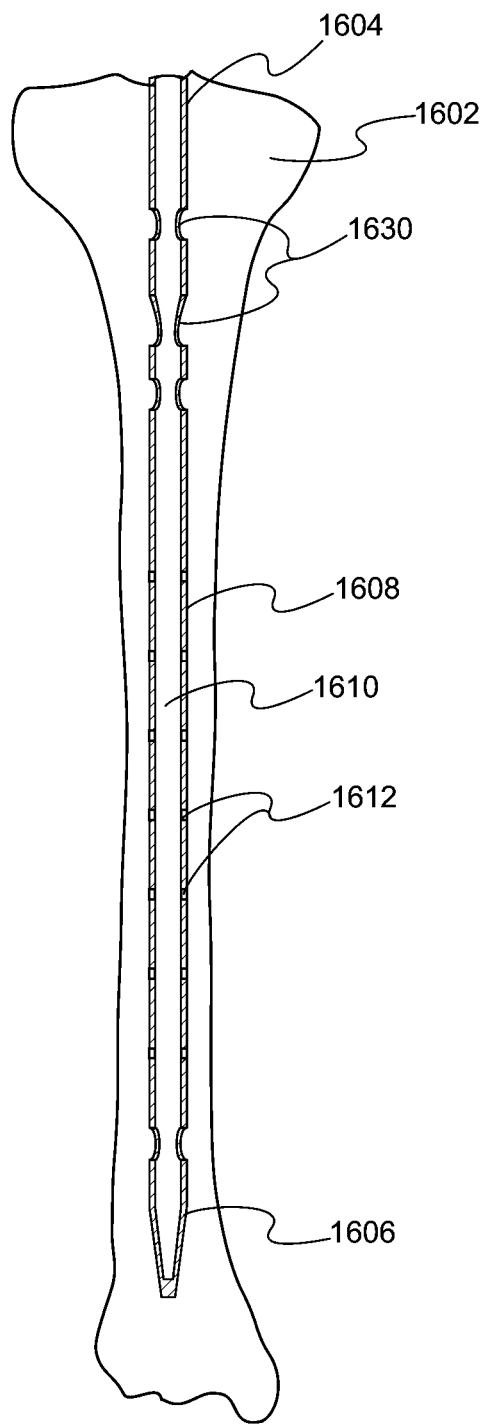
FIG. 17 shows a cross-sectional view of the fixation nail of FIG. 16.
Figure 18:
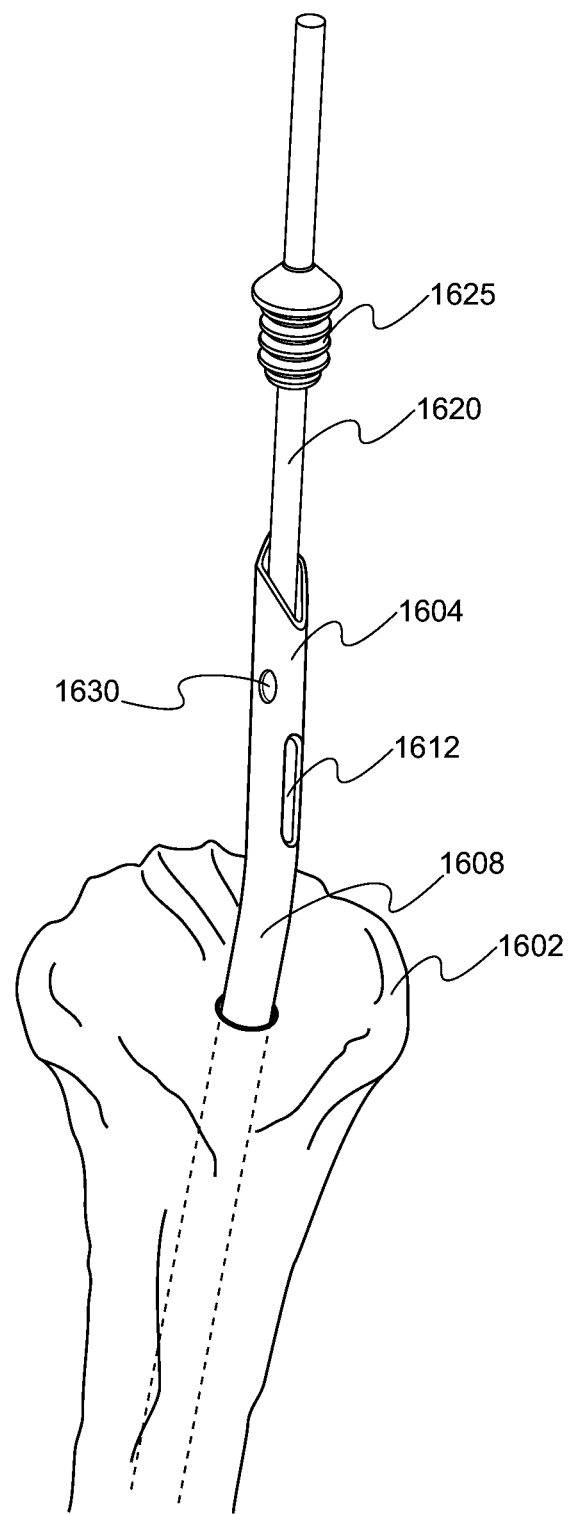
FIG. 18 shows a perspective view of the fixation nail of FIG. 16.

Referring now to FIG. 16, there is disclosed a tibia fixation nail 1600 disposed within a tibia 1602. The fixation nail has two ends 1604 and 1606 connected by a shaft 1608. The fixation nail includes a cannulated portion 1610, which is best seen in the cross-sectional view of FIG. 17, and fixation nail fenestrations 1612 along the length of the cannulated portion 1610. One end of the cannulated portion 1610 of the fixation nail 1600 may be configured to accept a nail insert. This is demonstrated in FIG. 18 which shows a perspective view of the a nail insert 1620 being inserted into the cannulated portion 1610 of the fixation nail 1600. The fixation nail 1600 has internal threads (not shown) on one end of its cannulated portion 1610 to promote fixation of the nail insert 1620 which also has threads 1625 on one end. As shown in the figures, the fixation nail need not be straight along its entire length, but may include one or more angles to facilitate the placement of the nail into a bone. The fixation nail may define one or more bores 1630 through its length through which fixation screws 1640, 1642, 1644 and 1646 may be passed in order to affix the fixation nail to the bone. The fixation screws may pass through the fixation nail substantially perpendicular to the long axis of the nail or they may pass through the nail at acute or obtuse angles with respect to the long axis of the nail. The bores may be aligned substantially parallel with respect to one another, substantially perpendicular with respect to one another or may be aligned at angles between parallel and perpendicular.

Figure 19:
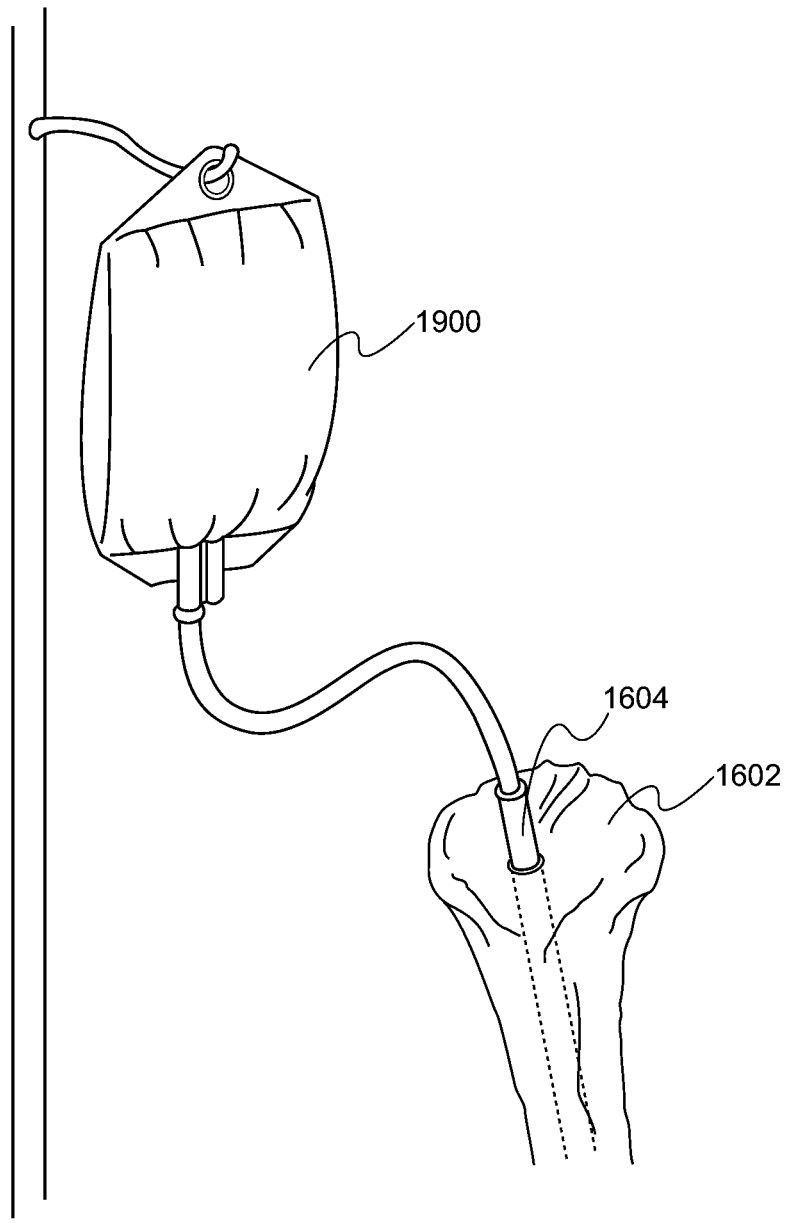
FIG. 19 shows a perspective view of an IV being used to provide a liquid to the fixation nail of FIG. 16.
Figure 20:
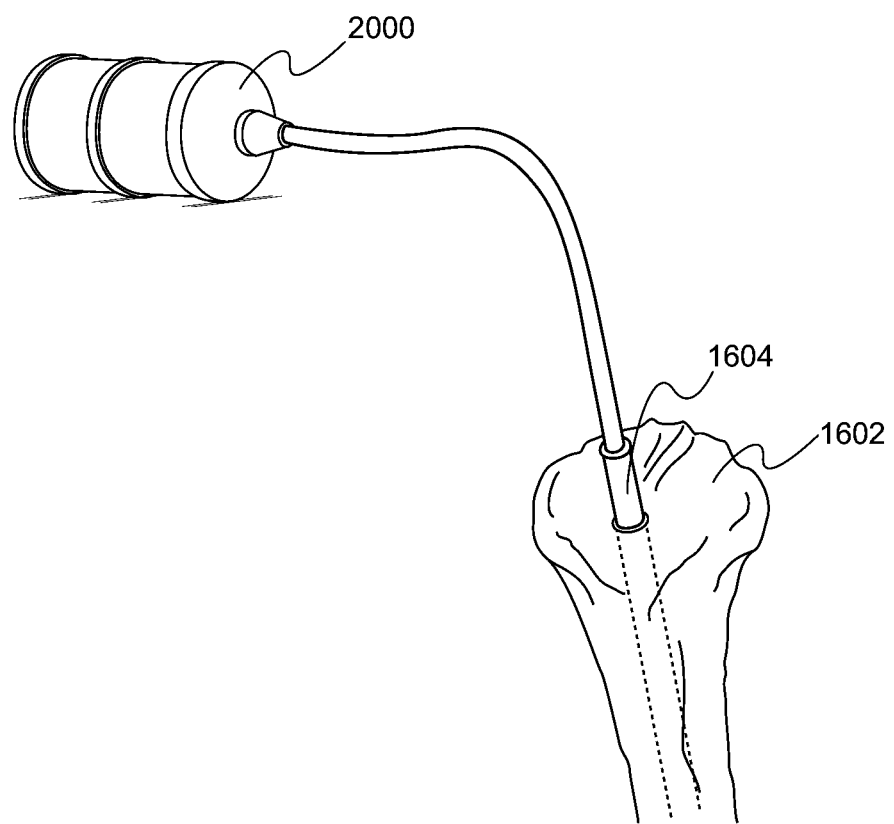
FIG. 20 shows a perspective view of a pump assembly being used to provide a liquid to the fixation nail of FIG. 16.

As discussed above, in certain applications it may be desirable that the substance to be delivered to the bone be stored in a reservoir prior to delivery. FIG. 19 discloses one illustrative embodiment of the invention in which an IV 1900 serves as a reservoir for delivering a substance to a tibia via the fixation nail of FIG. 18. FIG. 20 discloses an alternative embodiment where a pump 2000 serves as the reservoir for delivering a substance to a tibia via the fixation nail of FIG. 18.

In one embodiment of the invention, the delivery pathway between one or more insert fenestrations and one or more bone screw fenestrations is defined by two balloons, each of which is inflated between the outside of the insert and the inside of the bone screw to form a seal between the insert and the bone screw. This embodiment is exemplified in FIGS. 21 and 22. FIG. 21 shows a bone screw insert 2100 having a fenestration 2110 along its length. A first balloon 2120 is disposed around the outside of the insert 2100 above the fenestration 2110 and a second balloon 2130 is disposed around the outside of the insert 2100 below the fenestration 2110. The insert optionally has threads 2140 at one end that interlock with bone screw threads 2150 in a bone screw 2160 to help fix the insert 2100 into the bone screw 2160. The first and second balloons may be inserted into a bone screw in a deflated state. As shown in FIG. 22, when the insert is in place inside the bone screw the balloons 2120 and 2130 are disposed above and below one or more fenestrations 2170 in the bone screw. Once the insert is in place, the balloons may be inflated to form a seal between the outside 2180 of the insert 2100 and the inside 2190 of the bone screw 2160, isolating the insert fenestration 2110 and the bone screw fenestrations 2170 between the balloons. In this manner, the balloons help to define a delivery pathway between one or more insert fenestrations and one or more bone screw fenestrations.

Figure 23:
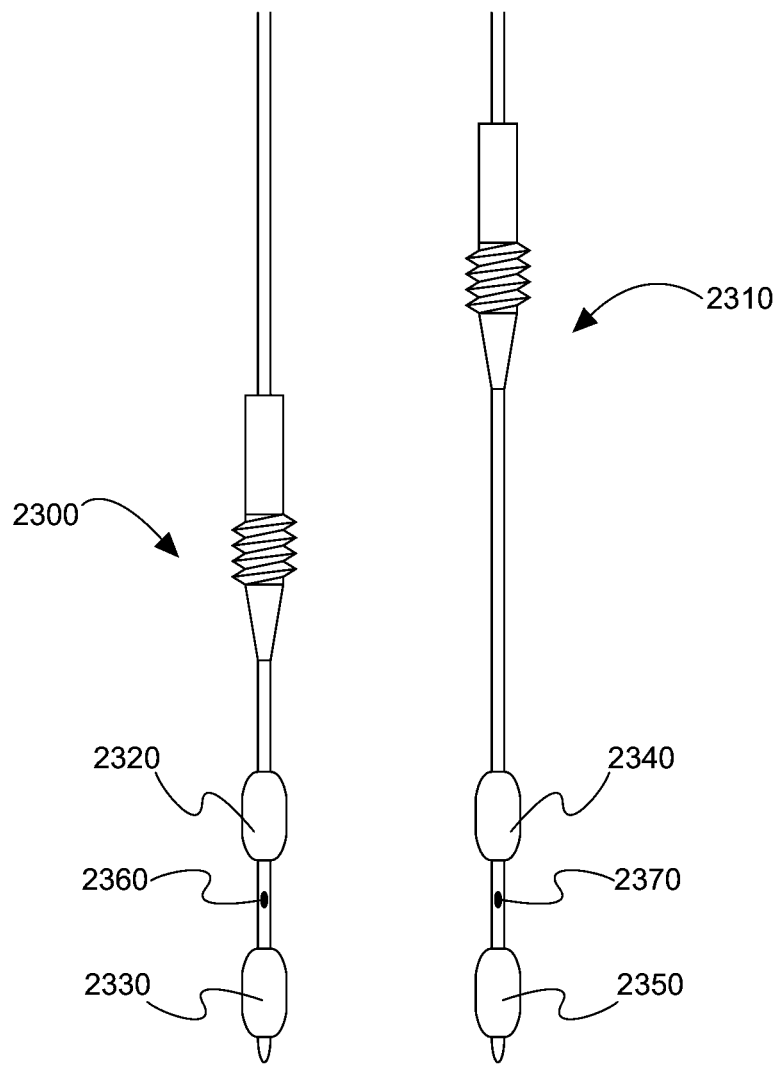
FIG. 23 shows two inserts of different lengths having balloons disposed around their shafts.

FIG. 23 shows two different bone-screw inserts 2300 and 2310, each having a pair of balloons 2320, 2330 and 2340, 2350 disposed along its length and situated above and below an insert fenestration 2360 and 2370. The bone-screw inserts have different lengths, such that they may be adapted for insertion into bone screws of different lengths or may be used to isolate fenestrations at different locations along the shaft of a given bone screw. Although the insert and bone screw fenestrations of FIGS. 21-23 are isolated between two inflated balloons, it should be understood that other configurations are possible. For example, one or more insert fenestrations and one or more bone screw fenestrations could be isolated between a single inflated balloon and the top end or the bottom end of the bone screw.

Figures 24A, 24B:
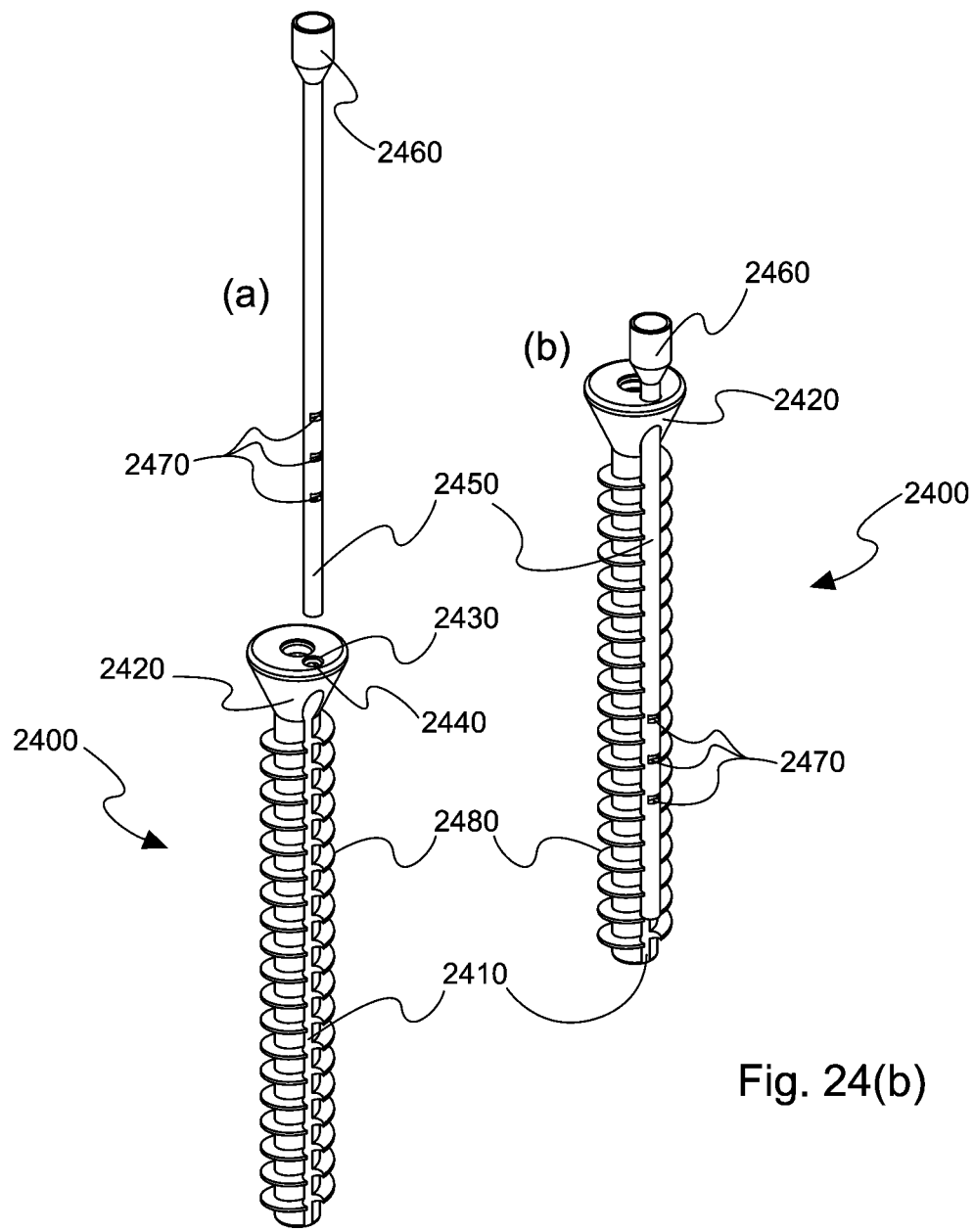
FIG. 24(a) shows a perspective view of a bone screw having and external groove along its length and a fenestrated insert adapted to fit into the groove.
FIG. 24(b) shows a perspective view of the insert of FIG. 24(a) inserted into the groove along the bone screw of FIG. 24(a).
Figure 25:
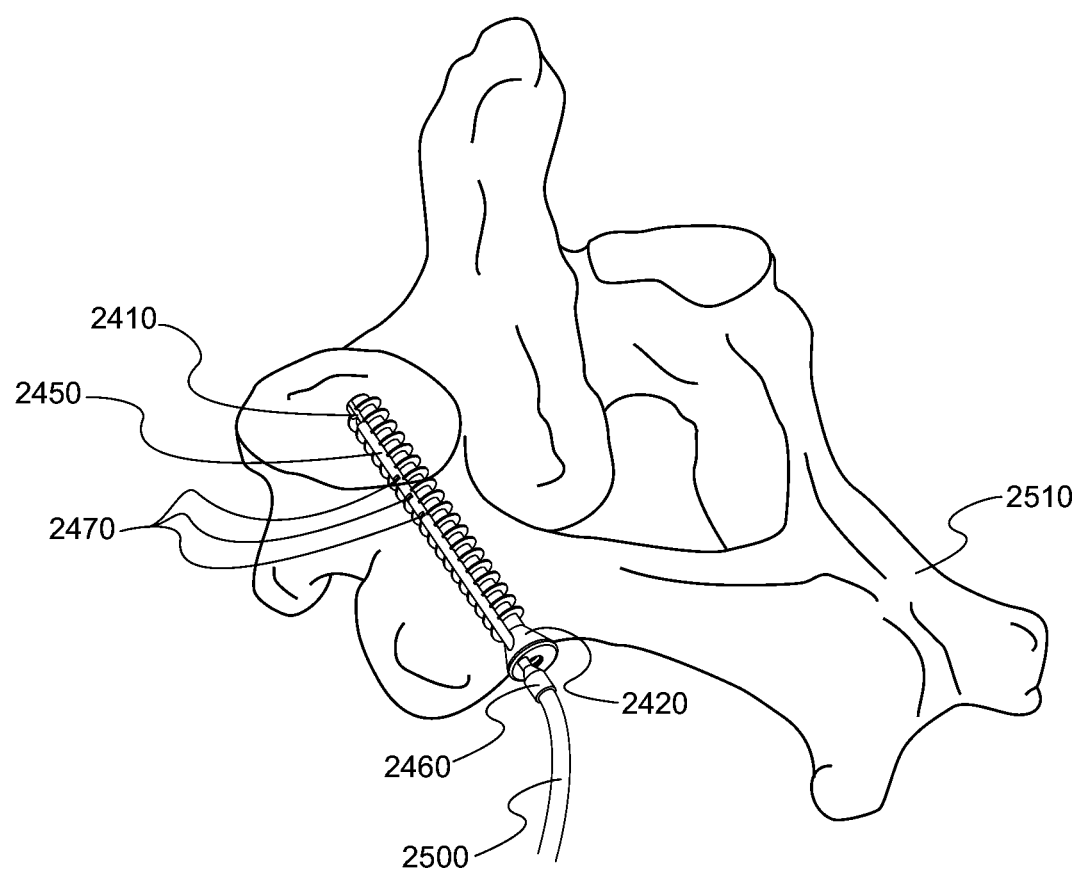
FIG. 25 shows the bone screw and insert of FIG. 24(b) inserted into the hip bone of a patient.

An alternative design for a substance delivery device is shown in FIGS. 24a and b. In this device a bone screw 2400 is provided with an attachment mechanism, shown as an exterior groove 2410, running along its length. The bone screw includes a head 2420 that defines a longitudinal bore 2430 having internal threads 2440. A cannulated insert 2450 adapted to fit through the longitudinal bore 2430 and into the groove 2410 is also provided. The insert includes a head 2460 adapted to accept a tube (not shown), or similar means for delivering a substance, and a plurality of fenestrations 2470 along its length. As shown in FIG. 24b, once in place, the insert provides substance delivery pathways along the bone screw from the cannulation at the head 2460 of the insert 2450 through the fenestrations 2470. In this illustrative embodiment, the insert 2450 does not extend beyond the threads 2480 of the bone screw 2400. Although not shown in FIG. 24, the insert may optionally include threads at one end, for example at the bottom of the insert head 2460, to engage the internal threads 2440 in the bone screw head 2420 to promote fixation of the insert. FIG. 25 shows a perspective view of the delivery device of FIG. 24 connected to a substance delivery tube 2500 and inserted into the hip bone 2510 of a patient.

Figures 26A, 26B:
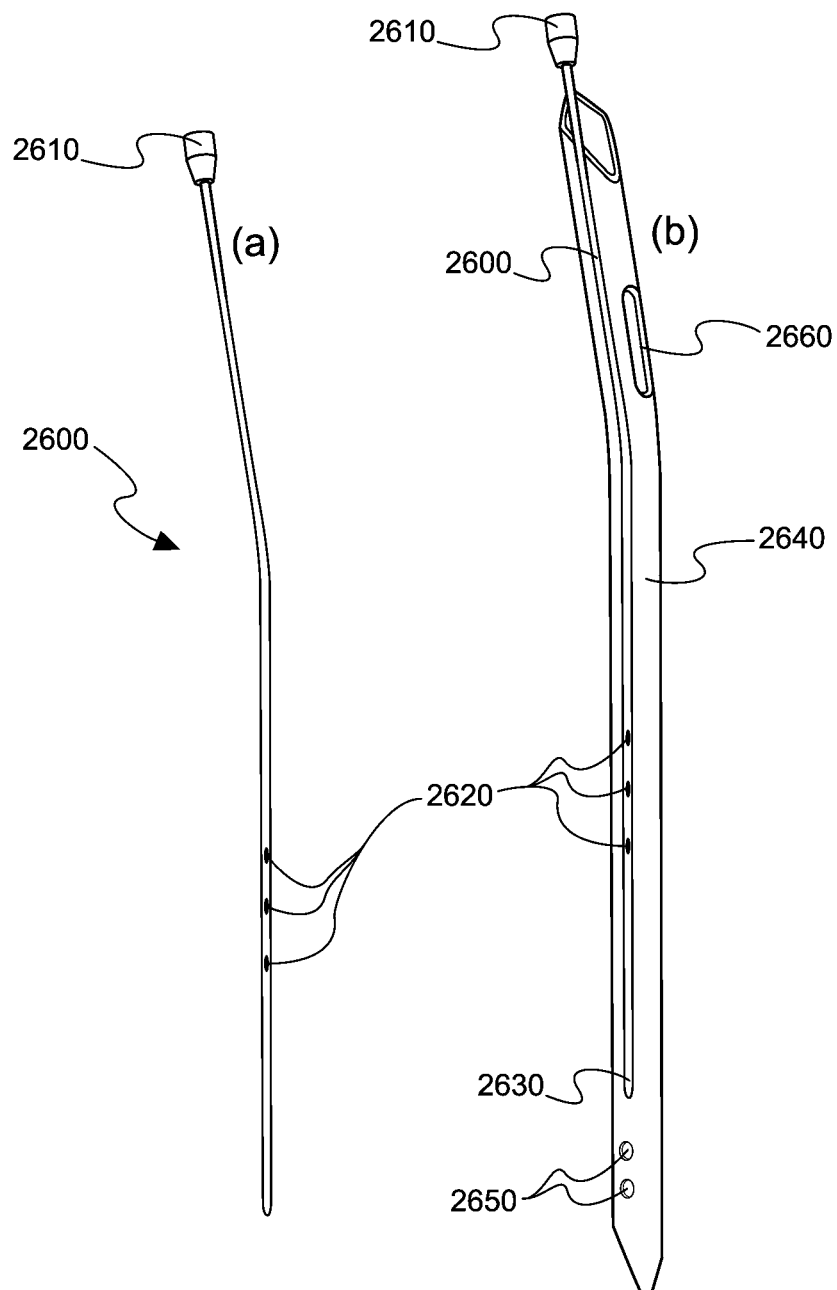
FIG. 26(a) shows a perspective view of an insert adapted to fit into a groove along fixation nail.
Figure 27:
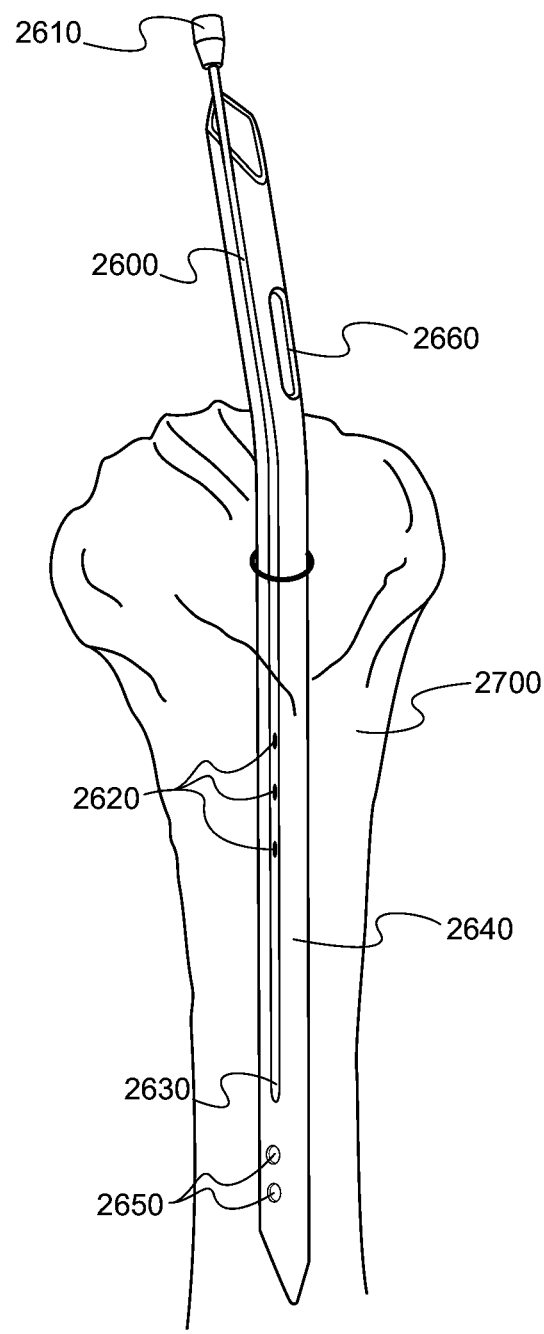
FIG. 27 shows the fixation nail and insert of FIG. 26(*b*) inserted into the tibia bone of a patient.

FIG. 26 depicts a substance delivery device, similar to that of FIG. 25, where an exterior insert is combined with a fixation nail. FIG. 26a shows a cannulated insert 2600 having a head 2610 adapted to receive a tube (not shown), or similar substance delivery means, at one end and a plurality of fenestrations 2620 along its length. As shown in FIG. 26b, the insert is adapted to fit into a groove 2630 running along the external surface of a fixation nail 2640. The fixation nail need not be straight along its entire length, but may include one or more angles to facilitate the placement of the nail into a bone. The fixation nail may define one or more bores 2650 through its length through which bone screws (not shown) may be inserted to fix the nail to the bone. In addition, the fixation nail may itself include one or more fenestrations 2660 along its length. FIG. 27 shows a perspective view of the delivery device of FIG. 26b inserted into the tibia 2700 of a patient.

Another aspect of the present invention is a method of administering a substance to a bone. In one embodiment, the method comprises introducing a cannulated, fenestrated bone screw into a bone, introducing a cannulated insert into the bone screw, and introducing a substance to be delivered into the cannulated portion of the insert. In another embodiment, the method comprises attaching a cannulated insert along at least a portion of an exterior surface of a bone screw, introducing the bone screw into a bone, and introducing a substance to be delivered into the cannulated portion of the insert. Under some circumstances, one may find it advantageous to introduce the insert into or along the bone screw, in its entirety or only partially, prior to introducing the bone screw into the bone. This sequence might be preferred in order to shorten the overall surgery time, or to reduce the amount of material that enters the bone-screw fenestrations from outside the screw during screw insertion, for example. Alternately, other circumstances may make it more advantageous to introduce the insert into the bone screw, in its entirety or only partially, after the bone screw is introduced into the bone. This latter sequence might be preferred in order to be able to determine which screw fenestrations or exterior insert attachment mechanisms (e.g. grooves) are located at the optimum location for delivery of the desired substance, and thus what insert configuration or length should be used to facilitate substance delivery to desired locations in or near a bone. Other sequences can be envisioned by one skilled in the art, such as for example, partially introducing the bone screw into a bone, partially or completely inserting the insert into or along the bone screw, and then completing the insertion of the bone screw into the bone. Even more sequence variations are possible when one considers the additional step of introducing the substance into the cannulated portion of the bone screw insert, and all such sequence variations are to be included within the scope of this disclosure.

In practicing the current invention it may also be found advantageous to drill a pilot hole in the one or more bones or bone pieces in order to facilitate introduction of the bone screw. In this regard it may be found advantageous to use bone screws with self-tapping threads, or to pre-cut the threads in the bone prior to bone screw insertion.

When the bone screw is a fixation screw, the present invention may further comprise the method of holding or fixing two or more bones or bone pieces in a fixed spatial relationship with respect to each other. Such a method may be desirable when it is desired to deliver a substance such as a medicant or therapeutic to the vicinity of a site where a peripheral skeletal fracture or an osteotomy is mended, a spondyloysis or an odontoid fracture repaired, or lumbar facet joints are fused.

The present invention may further comprise the method of delivering a substance to the vicinity of a bone including the steps of attaching a reservoir, a pump, or both, to the bone screws or bone-screw inserts disclosed herein. Such reservoirs and pumps may aid in the continuous, regulated, or long-term delivery of the desired substance to the vicinity of a bone, thereby facilitating the healing process or the overall health of the bone and its surrounding tissues.

The bone screw and insert embodiments disclosed herein may be configured to allow for re-sealing and multiple time or multiple use access to the cannulated portion of the bone screw or insert. In the exemplary embodiment of FIG. 28, a bone screw 2800 is shown inserted or disposed within a bone 2810. An insert 2820 is shown inserted within bone screw 2800. A seal, shown as an insert cap 2830, is coupled to the outer or proximal end of insert 2820. In the embodiment shown, insert cap 2830 is an end cap directly coupled to the inner surface of insert 2820. Insert cap 2830 acts to seal the outer or proximal end of insert 2820. In other embodiments, the seal may be positioned along the shaft of the insert. In some embodiments, cap 2830 is removably coupled to insert 2820, and in other embodiments, cap 2830 may be coupled to insert 2820 via a non-removable (i.e., permanent) coupling. A fluid delivery device, shown as syringe 2840, includes a needle 2850.

Figure 29A:
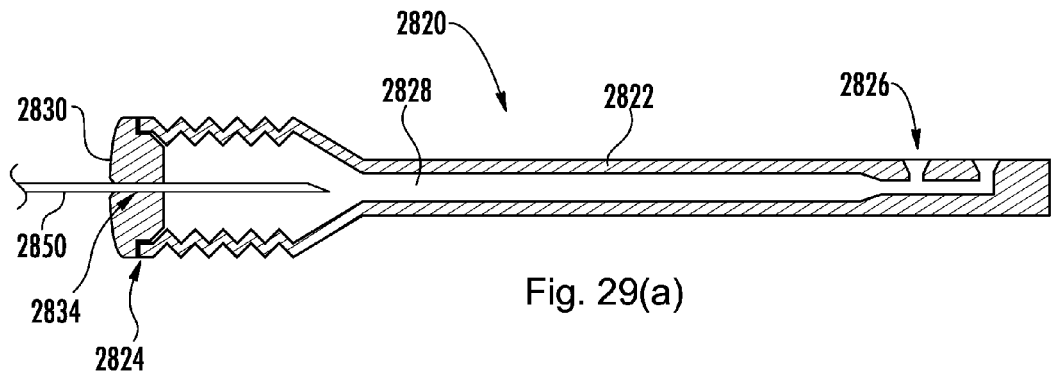
FIG. 29(*a*) shows a schematic cross-sectional view of a bone-screw insert with a resealing cap, according to an exemplary embodiment.
Figure 29B:
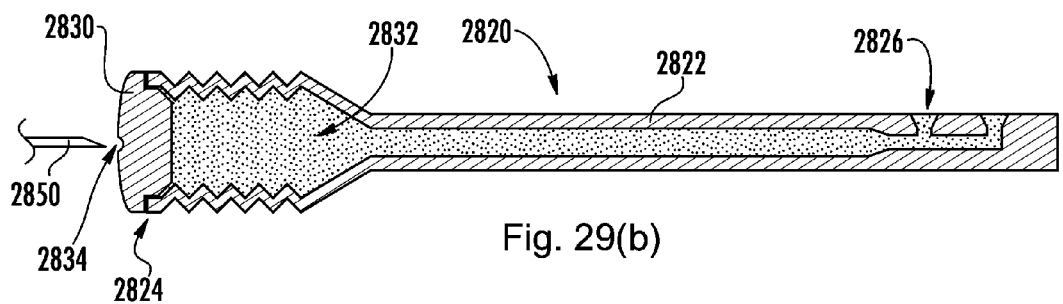

Referring to FIG. 29(a) and FIG. 29(b), a schematic cross-sectional view of insert 2820 is shown according to an exemplary embodiment. Insert 2820 includes a shaft 2822, an opening 2824 located at the proximal end of insert 2820, and at least one insert fenestration 2826 located through shaft 2822. The shaft 2822 of insert 2820 also includes a cannulation 2828 formed along at least a portion of shaft 2822. In the embodiment shown, opening 2824 is located at one end of cannulation 2828. As shown in FIG. 29(a) and FIG. 29(b), the opening 2824 of insert 2820 is closed or sealed by cap 2830. In this arrangement, cap 2830 includes an inner surface facing or in communication with cannulation 2828. Cap 2830 may be coupled to or attached to insert 2820 by any suitable means. For example, cap 2830 may be threaded to mate with threads located within opening 2824, and, in other embodiments, cap 2830 may be press fit into opening 2824 or may be attached to opening 2824 with an adhesive. In another embodiment, opening 2824 may be located along the sidewall of the insert, and cap 2830 may seal the opening along the sidewall of the insert.

As discussed above, a substance may be placed in the cannulated portion of an insert, such as insert 2820, so that the substance may be delivered through the insert fenestrations and through the bone screw fenestrations to the bone. In an exemplary embodiment, insert cap 2830 is able to provide multiple-time or reusable access to cannulation 2828 of the insert following implantation of the bone screw/insert combination into the bone. In the exemplary embodiment of FIG. 29(a) and FIG. 29(b), reusable, post-implantation access to cannulation 2828 of insert 2820 is provided by self-sealing cap 2830. In this embodiment, cap 2830 comprises a resilient, self-sealing material, and needle 2850 pierces through cap 2830 providing access to cannulation 2828. As shown in FIG. 29(a), needle 2850 creates a perforation 2834 that extends through cap 2830. With needle 2850 located within cannulation 2828, a substance 2832 may be delivered from the fluid delivery device into cannulation 2828. With substance 2832 within cannulation 2828, the substance may be delivered through insert fenestrations 2826 and through bone screw fenestrations as discussed in the various embodiments above.

Figure 28:
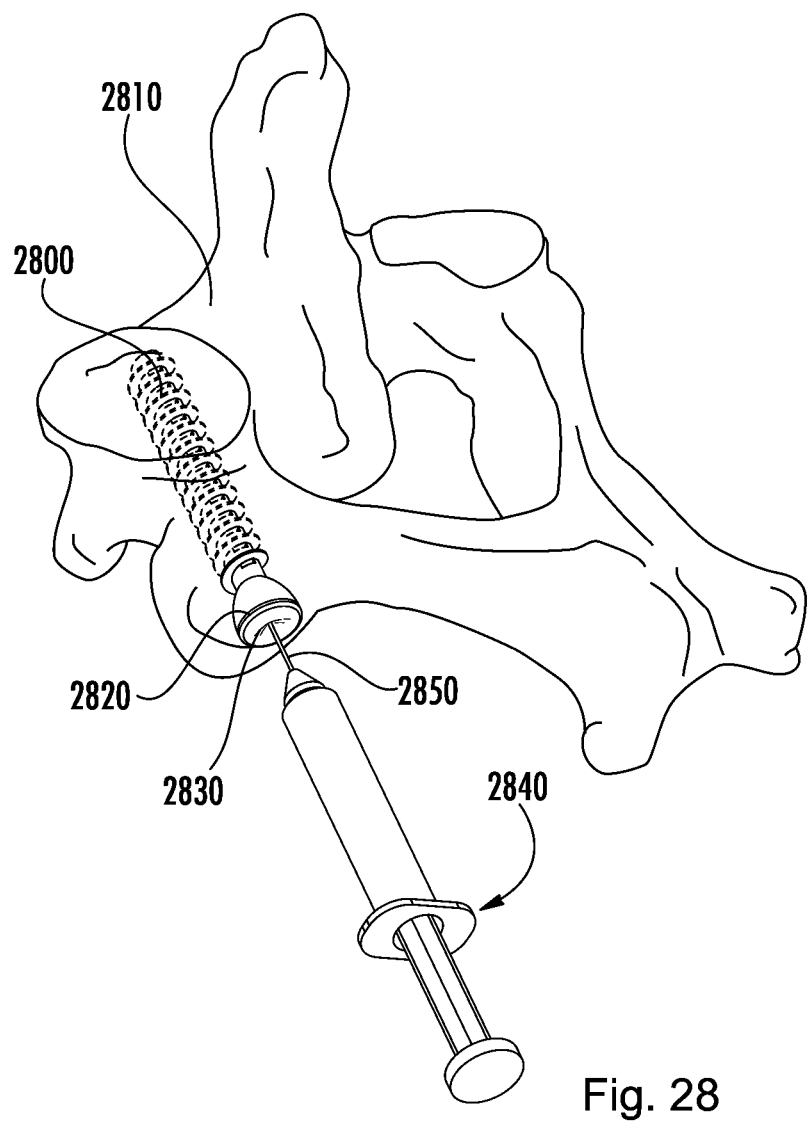
FIG. 28 shows a bone screw and an insert disposed in a bone and a perspective view of a syringe being used to provide a substance to the bone screw, according to an exemplary embodiment.

As shown in FIG. 29(b), once substance 2832 is delivered to insert 2820, needle 2850 may be removed or withdrawn from cap 2830. Once needle 2850 is withdrawn, perforation 2834 self-seals to prevent substance 2832 from flowing out of the proximal end of insert 2820 through perforation 2834. The process of inserting needle 2850 through cap 2830 may be repeated as necessary to deliver multiple doses of a substance to insert 2820. While the fluid delivery device is shown in FIG. 28 as syringe 2840, in various other embodiments, needle 2850 may be connected to a variety of fluid delivery devices. For example, the fluid delivery device may be a pump (e.g., an infusion pump) or a bag or reservoir or fluid bag (similar to an IV bag) coupled to needle 2850 via tubing. In one embodiment, the fluid delivery device may be a micro-infusion device in fluid communication with the cannulated portion of the insert and/or bone screw. In this embodiment, the micro-infusion pump may be worn by a user, and a substance may be continuously delivered through the bone screw and/or insert to promote bone growth.

In various embodiments, cap 2830 may be made from any material or combination of materials that provides for resealing or self-sealing. In various embodiments, cap 2830 may be made from a compliant, non-rigid or resilient material that resiliently expands following withdrawal of needle 2850 to seal perforation 2834 caused by needle 2850. In one embodiment, cap 2830 may be made from a surgical, self-sealing rubber or polymer, such as surgical silicone rubber.

The post-implantation access to cannulation 2828 of insert 2820 provided by cap 2830 may allow the user to deliver a new or second substance or additional doses of a same substance to the bone as needed to treat a particular patient. For example, following implantation of the bone screw/insert combination, separate doses of antibiotics may be delivered to a fracture site via insert 2820. In another embodiment, insert 2820 may be used for repeated delivery of cancer treating drugs (e.g., anti-cancer drugs) to the bone in which the bone screw is implanted. In another embodiment, bone morphogenic proteins may be delivered in separate doses to the bone via insert 2820. In other embodiments, any other substance that may be intermittently delivered to a patient may be delivered using insert 2820. Further, in contrast to single-use delivery devices, repeatable access and multiple time delivery via insert 2820 may be useful in adjusting or changing the substances delivered via insert 2820. For example, insert 2820 and resealing cap 2830 allow the user to change either the dose or the type of substance delivered to a patient each time needle 2850 is inserted through cap 2830. In addition, post-implantation access to cannulation 2828 of insert 2820 by needle 2850 may allow for the post-implantation connection of any desired fluid delivery device (e.g., an IV or infusion pump) to the insert by connecting the fluid delivery device to needle 2850. This may allow the user to switch or change the type of fluid delivery device used to deliver fluid to the bone via the bone screw/insert combination. In other embodiments, needle 2850 may also be connected to a material removal device allowing for repeat and resealing access through cap 2830 for removal of material from cannulation 2828 of insert 2820, as described below in relation to FIGS. 30(a) and 30(b).

To deliver a dose of substance to a patient by piercing cap 2830 with needle 2850, the user will need to align needle 2850 with cap 2830 following implantation of the implanted bone screw/insert combination. In some embodiments, the bone screw/insert combination may be located a small distance below the skin such that cap 2830 may be palpated through the skin allowing the user to align the needle with cap 2830 by touch. In other embodiments, the bone screw/insert combination may be located in a bone deeper below the skin such that alignment via palpation may be difficult or impossible. In such an embodiment, needle 2850 may be aligned with cap 2830 by imaging the location of the cap 2830 via a suitable imaging device (e.g., via X-ray, CT, etc.).

Figure 29C:
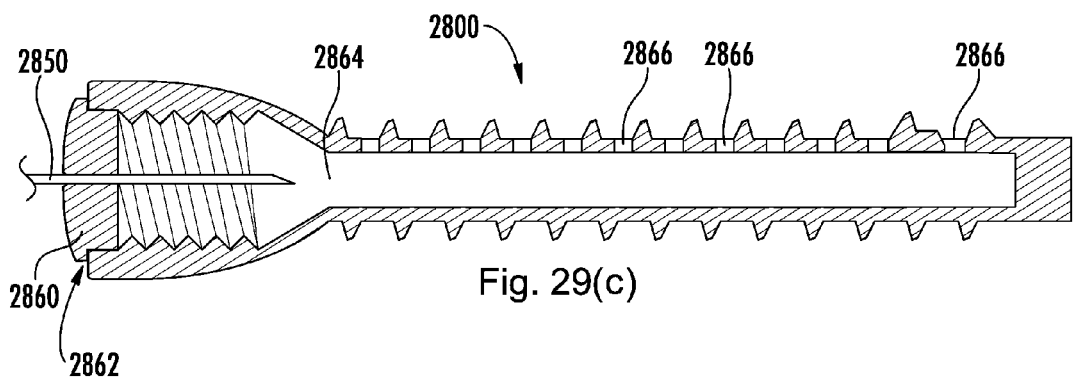

While the embodiment shown in FIGS. 28, 29(a) and 29(b) shows the resealing cap coupled to an insert, it should be understood that in other embodiments cap 2830 may be coupled directly to a cannulated bone-screw to seal the proximal opening of a bone-screw. For example, as shown in FIG. 29(c), bone screw 2800 may include a resealing cap, shown as bone screw cap 2860 (similar to cap 2830), that is coupled to or attached to bone screw 2800 such that bone screw cap 2860 seals the proximal opening 2862 of bone screw 2800. Similar to the other bone screw embodiments discussed herein, bone screw 2800 includes a bone screw cannulation 2864 and bone screw fenestrations 2866. With needle 2850 extending through cap 2860, material may be delivered to a bone through bone screw fenestrations 2866, and, as discussed below, material may be removed from the bone through bone screw fenestrations 2866. As shown in FIG. 29(c), bone screw cap 2860 may seal bone screw 2800 without an insert disposed within a bone screw cannulation 2864. In another embodiment, bone screw cap 2860 may seal the proximal opening 2862 of bone screw 2800 with an insert disposed within bone screw cannulation 2864. Further, it should be understood that various embodiments of resealing caps 2830, 2860 may be used with any of the bone screw and insert embodiments discussed herein.

Figures 30A, 30B:
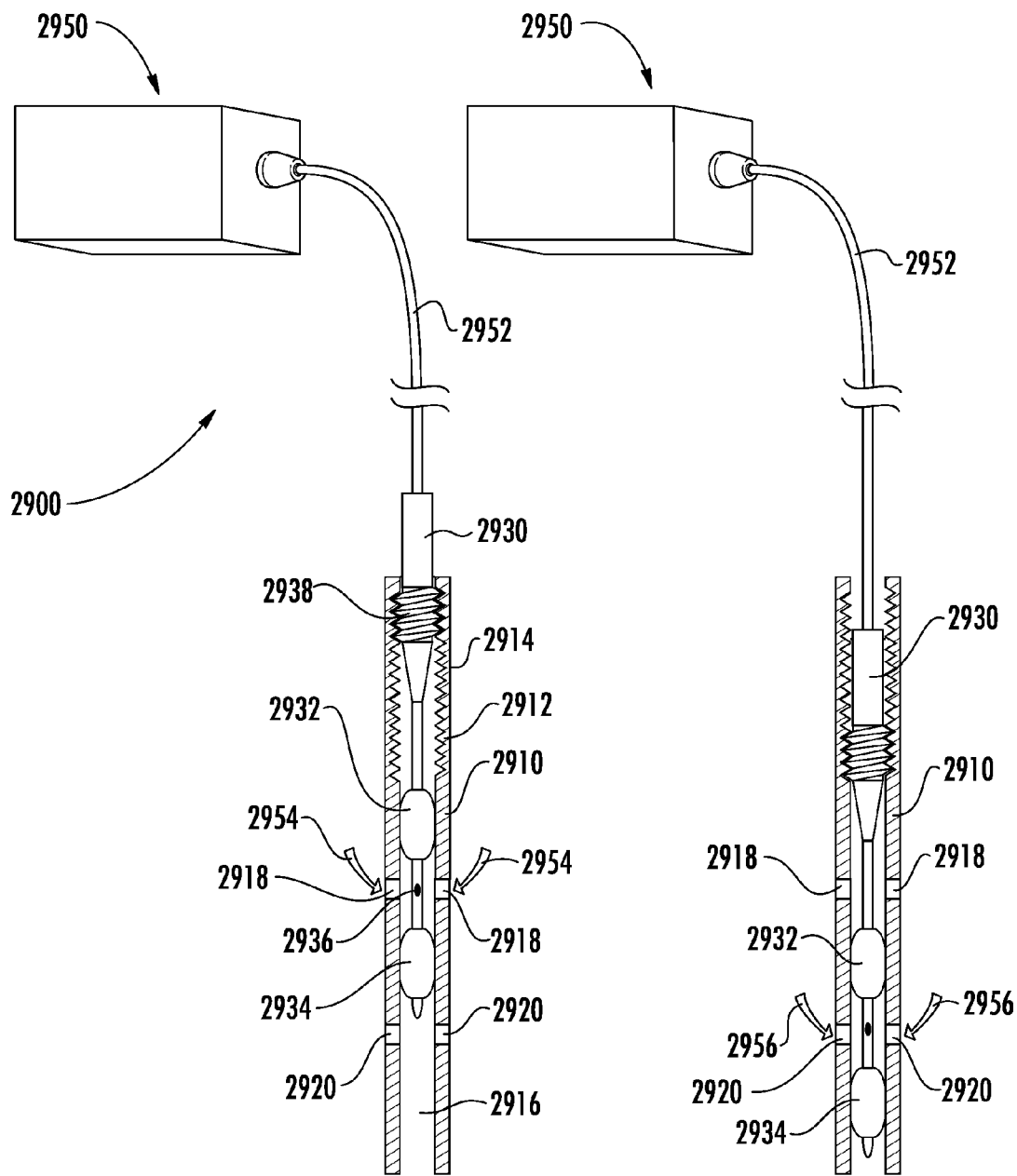
FIG. 30(*a*) shows a schematic cross-sectional view of an insert as part of a material removal system, according to an exemplary embodiment.

In other embodiments, the bone screw and insert embodiments disclosed herein may be used as part of a material or tissue removal system. In the exemplary embodiment of FIG. 30(a) and FIG. 30(b), a material removal system 2900 is shown according to an exemplary embodiment. Material removal system 2900 includes a bone screw 2910, a bone screw insert 2930 and a material removal device, shown as suction device 2950 (e.g., a pump, vacuum, etc.). Bone screw 2910 includes a sidewall 2912, a threaded portion, shown as threads 2914, formed on the inner surface of sidewall 2912, and a bone screw cannulated portion 2916. Bone screw 2910 also includes at least first fenestrations 2918 and second fenestrations 2920. In the orientation of FIG. 30(a), fenestrations 2918 are located above (i.e., closer to the proximal end of bone screw 2910) fenestrations 2920.

Insert 2930 includes a first expandable portion, shown as first balloon 2932, and a second expandable portion, shown as second balloon 2934. Insert 2930 includes an insert fenestration 2936 located between balloons 2932 and 2934. As discussed above regarding FIGS. 21-23, balloons 2932 and 2934 may be inflated to form seals with the inner surface of bone screw 2910 to provide for isolation of one or more of the bone screw fenestrations. Insert 2930 includes a threaded portion, shown as threads 2938, that engages with threads 2914 of bone screw 2910. While material removal system 2900 is shown and described with an insert that includes expandable sections, it should be understood that material removal system 2900 may utilize any of the bone screw/insert combinations discussed herein.

Material removal system 2900 includes a material removal device, shown as suction device 2950, connected to insert 2930 via a tubing 2952. Suction device 2950 is configured to extract or aspirate material from cannulated portion 2916 of the bone screw and from the area surrounding the bone screw. In various embodiments, suction device 2950 may be a motorized suction device or may be a manual suction device (e.g., a syringe). In the embodiment shown in FIG. 30(a), balloons 2932 and 2934 are inflated to isolate fenestrations 2918. As illustrated by arrows 2954, suction device 2950 applies a vacuum to insert 2930 via tubing 2952 such that material is drawn in through fenestrations 2918 and is moved through the insert and tubing to reach the suction device. Thus, in this manner, suction device 2950 allows for removal or harvesting of material adjacent fenestrations 2918.

Various types of material may be removed from a patient using material removal system 2900. In addition, material may be removed for various purposes, including for diagnostic testing and/or for subsequent implantation. For example, in one embodiment, bone marrow may be harvested using material removal system 2900 to be used for bone marrow donation or for diagnostic testing. Other materials, such as blood, may be removed for diagnostic testing. In some embodiments, various materials may be removed from the bone screw using suction device 2950 to test for the presence of infection within the bone at the site of implantation of the bone screw.

In one embodiment, material removal system 2900 may be used to harvest osteoprogenitor cells from the bone of the patient into which bone screw 2910 is inserted. In one such embodiment, the harvested osteoprogenitor cells harvested using material removal system 2900 may then be implanted into another area of the patient (e.g., another bone) where bone growth is desired. In one specific embodiment, material removal system 2900 may be used to remove osteoprogenitor cells from one location in a patient, and then the removed osteoprogenitor cells may be implanted using one of the bone screw/insert combinations discussed herein located at another position within the patient. In various embodiments, the osteoprogenitor cells may be combined with other materials (e.g., calcium phosphate, hydroxylapatite, demineralized bone matrix, etc.) that may facilitate or enhance bone growth that results from the osteoprogenitor cells.

As shown in FIG. 30(a) and FIG. 30(b), bone screw 2910 includes a plurality of fenestrations (e.g., fenestrations 2918 and 2920). As used as part of material removal system 2900, insert 2930 and the plurality of fenestrations of bone screw 2910 allow the user to select or to isolate individual fenestrations or groups of fenestrations to selectably harvest material through the selected fenestrations. For example, in FIG. 30(a), insert 2930 is shown harvesting material through fenestrations 2918. In FIG. 30(b), insert 2930 is shown positioned within bone screw 2910 such that fenestrations 2920 are isolated between balloons 2932 and 2934. In this position, operation of suction device 2950 allows for removal of material through fenestrations 2920, as depicted by arrows 2956. This arrangement allows the user to selectively take samples of removed material from various positions within the bone.

In one embodiment, insert 2930 may include a resealing cap, such as cap 2830, that allows suction device 2950 to be connected to the cannulated portion of the insert via a needle, such as needle 2850. In other embodiments, the material removal device may be a device other than a suction-based aspiration device. For example, the material removal device may be any other suitable material removal device such as an absorbent device (e.g., a swab) that absorbs material located within either the cannulated portion of the bone screw or the insert.

Figure 31:
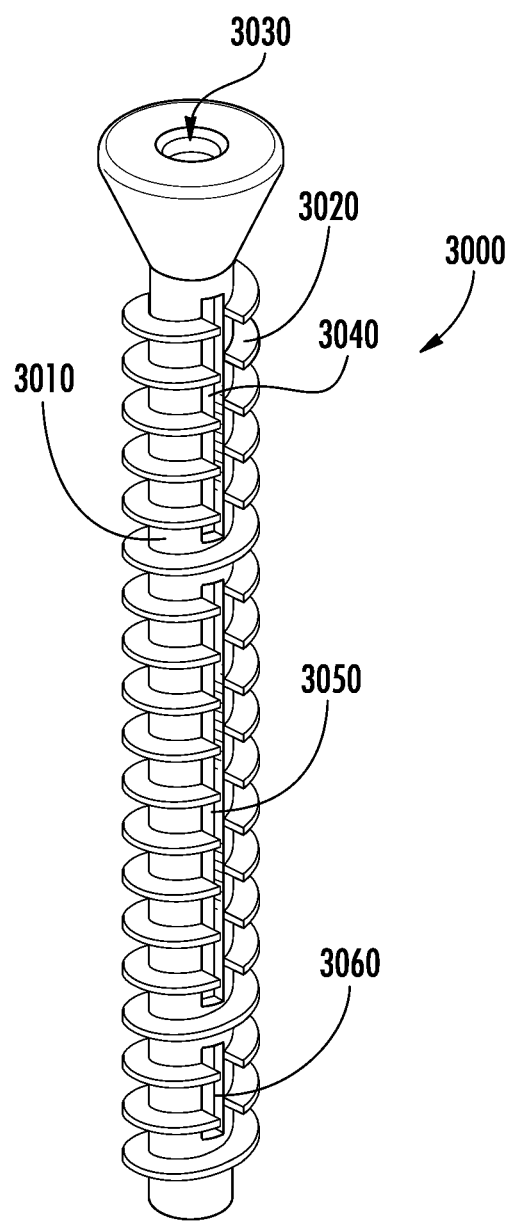
FIG. 31 shows a perspective view of a bone screw including slot-shaped fenestrations, according to an exemplary embodiment.

In other embodiments, a bone screw may include one or more fenestrations shaped as a slot extending longitudinally along the shaft of a bone screw. Referring to FIG. 31, bone screw 3000 is shown according to an exemplary embodiment. Bone screw 3000 includes a shaft 3010 and bone screw threads 3020. Bone screw 3000 includes a cannulation 3030, a first fenestration 3040, a second fenestration 3050, and a third fenestration 3060. First fenestration 3040 and second fenestration 3050 are configured as rectangular slots that extend in the longitudinal direction along shaft 3010. In the embodiment shown, the length of first fenestration 3040 in the longitudinal direction is approximately a quarter of the longitudinal length of shaft 3010 and the length of second fenestration 3050 in the longitudinal direction is approximately half of the longitudinal length of shaft 3010. Third fenestration 3060 is shown as a smaller slot-shaped fenestration located near the distal end of bone screw 3000.

In other embodiments, fenestrations, such as fenestrations 3040, 3050 and 3060, may be of other lengths relative to shaft 3010 (e.g., ⅛ of the length of shaft 3010, ¼ of the length of shaft 3010, ½ of the length of shaft 3010, and ¾ of the length of shaft 3010, etc.). In the embodiment shown in FIG. 31, threads 3020 are shown including gaps or spaces at the location of fenestrations 3040, 3050 and 3060. In other embodiments, threads 3020 may be contiguous threads that extend above or overlap fenestrations 3040, 3050 and 3060.

Figure 32:
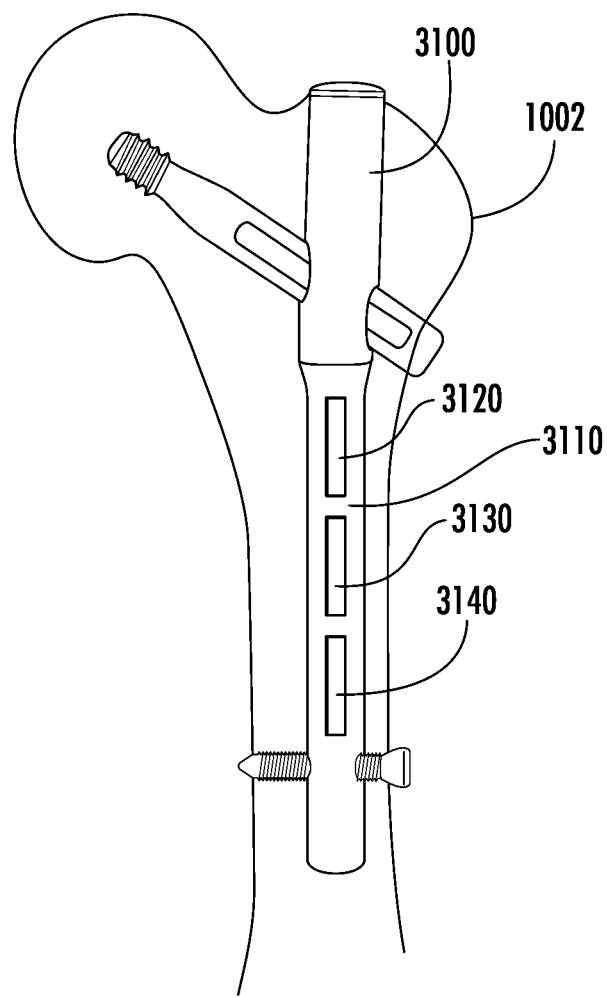
FIG. 32 shows a fixation nail including slot-shaped fenestrations inserted into the femur bone of a patient, according to an exemplary embodiment.

Referring to FIG. 32, a femur fixation nail 3100 disposed within a femur 1002 is shown. Fixation nail 3100 includes a shaft 3110 which is cannulated. Fixation nail 3100 is similar to fixation nail 1000 shown in FIG. 10 except that fixation nail 3100 includes three rectangular-shaped slot fenestrations 3120, 3130 and 3140 that extend in the longitudinal direction along shaft 3110. In the embodiment shown, all of the fenestrations 3120, 3130 and 3140 are generally of the same size and shape.

It should be understood that while FIGS. 31 and 32 show two bone screw embodiments including slot-shaped fenestrations, any of the bone screw embodiments discussed herein may include one or more slot-shaped fenestrations. Further, while the bone screw embodiments of FIGS. 31 and 32 show bone screws having three slot-shaped fenestrations, it should be understood that the bone screw embodiments may include any number of slot-shaped fenestrations (e.g., 1, 2, 4, 5, 6, 7, 8, etc.) as needed for a particular application, procedure, patient, etc. While in the exemplary embodiments the slot-shaped fenestrations are shown as rectangular in shape, other shapes may be used (e.g., oval, elliptical, diamond, triangular, etc.). Further, while FIGS. 31 and 32 depict slot-shaped fenestrations with longitudinal axes extending in the direction of the longitudinal axis of the shaft of the bone screw, slot-shaped fenestrations may assume other positions or orientations relative to the shaft of the bone screw. In one exemplary embodiment, a slot-shaped fenestration may be a circumferentially oriented fenestration such that the longer axis of the fenestration is perpendicular to the longitudinal axis of the shaft (as shown in FIG. 10).

Figures 33A, 33B, 33C:
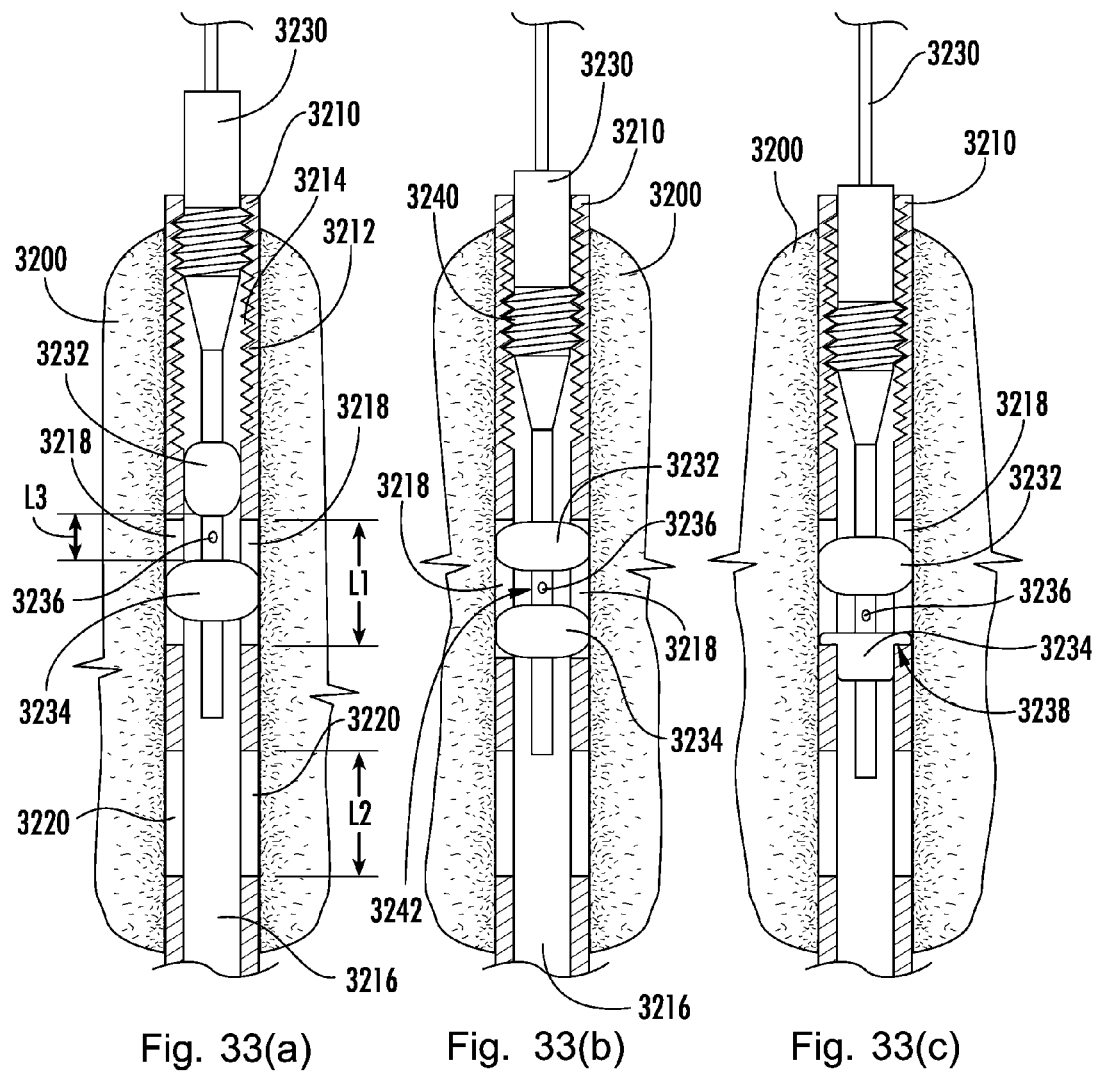
FIG. 33(*a*) shows a schematic cross-sectional view of an insert disposed in a first position within a bone screw, according to an exemplary embodiment.

Referring to FIG. 33(a), FIG. 33(b) and FIG. 33(c), a bone screw 3210 is shown implanted or disposed within a bone 3200. Bone screw 3210 includes a sidewall 3212, a threaded portion, shown as threads 3214, formed on the inner surface of sidewall 3212, and a bone screw cannulated portion 3216. As shown, bone screw 3210 includes first fenestrations 3218 and second fenestrations 3220. Fenestrations 3218 and 3220 are slot-shaped fenestrations that extend longitudinally along sidewall 3212. Bone screw 3210 may be a threaded bone screw, such as bone screw 3000, a fixation nail, such as femur fixation nail 3100, or any other bone screw embodiment disclosed herein. In the orientation of FIG. 33(*a*), fenestrations 3218 are located above (i.e., closer to the proximal end of bone screw 3210) fenestrations 3220.

An insert 3230 is shown positioned within cannulated portion 3216 of bone screw 3210. Insert 3230 includes a first expandable portion, shown as first balloon 3232, and a second expandable portion, shown as second balloon 3234. Insert 3230 includes an insert fenestration 3236 located between balloons 3232 and 3234. In the embodiment shown in FIGS. 33(*a*), 33(*b*) and 33(*c*), the longitudinal length, L1, of fenestrations 3218 and/or the longitudinal length, L2, of fenestrations 3220 are greater than the longitudinal length, L3, of the portion of insert 3230 that is located between first balloon 3232 and second balloon 3234.

The relative sizing of fenestrations 3218 and 3220 and the portion of the insert between the upper and lower balloons allows for selection or isolation of a portion of slot-shaped fenestrations 3218 and 3220. As shown in FIG. 33(*a*), insert 3230 may be positioned such that insert fenestration 3236 is located adjacent the upper ends of fenestrations 3218. With insert 3230 in this position, balloons 3232 and 3234 may be inflated to provide for isolation or selection of the upper portions of fenestrations 3218. With the upper portions of fenestrations 3218 isolated, a substance may be delivered through insert fenestration 3236 to the portion of bone 3200 adjacent the isolated section of fenestrations 3218, and/or a material may be removed from the portion of bone 3200 adjacent the isolated section of fenestrations 3218 via insert 3230, as discussed in the various embodiments above.

In general, upper balloon 3232 is expanded to form an upper seal between the outer surface of the balloon and the inner surface of the bone screw and/or the tissue adjacent the bone screw fenestration, and lower balloon 3234 is expanded to form a lower seal between the outer surface of the balloon and the inner surface of the bone screw and/or the tissue adjacent the bone screw fenestration. Thus, with the balloons expanded, the lower surface of upper balloon 3232 and the upper surface of lower balloon 3234 define a sealed chamber or section 3242 that isolates a portion of the adjacent bone screw fenestration. Insert fenestration 3236 is located within sealed section 3242, and thus, a pathway is defined between the portion of bone 3200 adjacent the sealed section 3242 and the proximal end of insert 3230. A substance may be delivered to bone 3200 via the pathway and/or a material may be removed from bone 3200 via the pathway as discussed above in the various embodiments.

Each of FIGS. 33(*a*), 33(*b*), and 33(*c*) show the isolation of various portions of fenestrations 3218 according to various exemplary embodiments. In the position shown in FIG. 33(*a*), upper balloon 3232 is expanded to form an upper seal with the inner surface of bone screw 3210 above fenestrations 3218, and lower balloon 3234 is expanded to form a lower seal with both the tissue (e.g., bone 3200) adjacent to fenestrations 3218 and with the inner surface of bone screw 3210 that is laterally adjacent to fenestrations 3218 (not visible in the section view of FIG. 33(*a*)). In the position shown in FIG. 33(*b*), both upper balloon 3232 and lower balloon 3234 are expanded to form seals with the tissue (e.g., bone 3200) adjacent to fenestrations 3218 and with the inner surface of bone screw 3210 that is laterally adjacent to fenestrations 3218 (not visible in the section view of FIG. 33(*b*)). In the position shown in FIG. 33(*c*), lower balloon 3234 is expanded to form a lower seal with the inner surface of bone screw 3210 below fenestrations 3218, and upper balloon 3232 is expanded to form an upper seal with both the tissue (e.g., bone 3200) adjacent to fenestrations 3218 and with the inner surface of bone screw 3210 that is laterally adjacent to fenestrations 3218 (not visible in the section view of FIG. 33(*c*)). Also as shown in FIG. 33(*c*), an upper portion of balloon 3234 is shown expanding to seal against the lower surface 3238 of fenestrations 3218 by expanding through laterally through fenestration 3218. It should be understood that, both balloons 3232 and 3234 may be configured to allow for expansion through the fenestrations to provide for sealing as shown in FIG. 33(*c*).

While FIGS. 33(*a*), 33(*b*), and 33(*c*) show three exemplary positions at which insert 3230 may be used to isolate portions of fenestrations 3218, it should be understood that insert 3230 may be moved to any position relative to the fenestration as desired by the user. In the embodiment shown, the positioning may be selected by advancing insert 3230 through threads 3214 of bone screw 3210 via cooperation of insert threads 3240. While FIGS. 33(*a*), 33(*b*) and 33(*c*) depict selection of various portions of fenestrations 3218, it should be understood that insert 3230 may be sized and configured such that portions of any fenestration of bone screw 3210 may be selected as discussed above.

Referring again to FIGS. 21-23, 30(*a*)-(*b*), and 33(*a*)-(*c*), one or more expandable portions of the associated insert 2100, 2300, 2930, 3230 are configured to expand laterally, such as by inflation or otherwise, to at least partially constrain adjacent fluid flow (e.g., to form seals, O-rings, annular boundaries; see, e.g., balloons 2120, 2130 as shown FIGS. 21-23; balloons 2932, 2934 as shown in FIGS. 30(*a*)-(*b*); and balloons 3232, 3234 as shown in FIGS. 33(*a*)-(*c*)).

In some embodiments, the expandable portions are configured to improve bone treatment by facilitating delivery of fluid to the bone, such as by directing fluid flowing from the insert to a particular fenestration (e.g., fenestration 2170 as shown in FIG. 21; fenestrations 2918 and 2920 as shown in FIGS. 30(*a*)-(*b*)) of an associated bone screw or to a particular portion of the bone. In other embodiments, the expandable portions are configured to facilitate controlled removal of fluid from a bone, such as by directing fluid flowing into and through the insert from a particular fenestration of an associated bone screw or from a particular portion of the bone.

Figure 34:
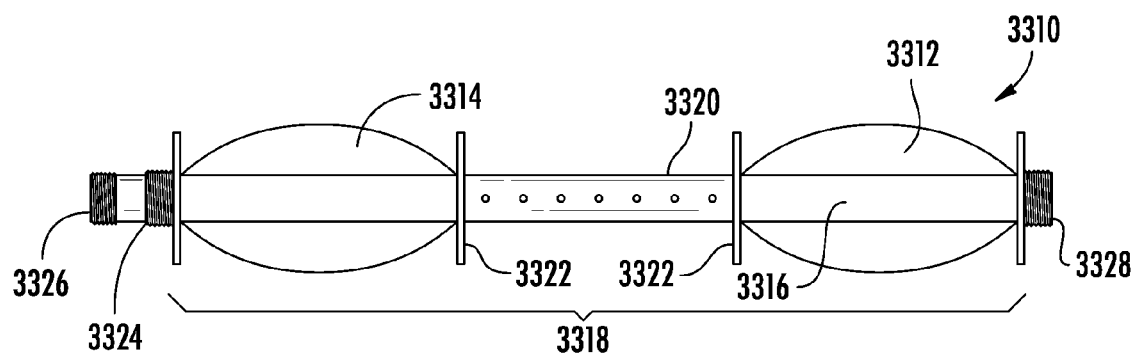
FIG. 34 is a schematic cross-sectional view of an assembly, such as an insert for the bone screw of FIG. 21, in a first configuration according to an exemplary embodiment.
Figure 35:
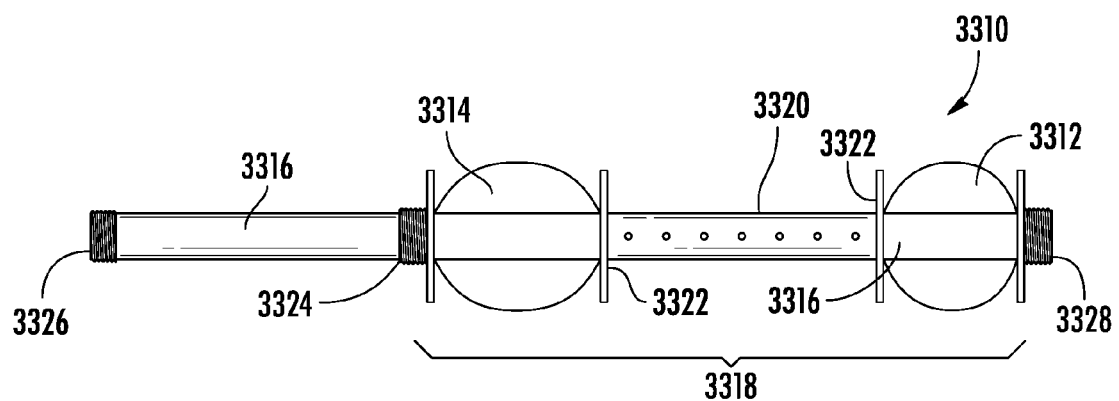
FIG. 35 is a schematic cross-sectional view of the assembly of FIG. 34 in a second configuration.

In contemplated embodiments, some expandable portions of the associated insert 2100, 2300, 2930, 3230 are inflatable, and may be inflated in various ways. In some embodiments, a inflatable balloon (e.g., balloons 2120, 2130 as shown FIGS. 21-23) is coupled to a conduit (e.g., fill tube) configured to deliver fluid (e.g., air, saline, etc.) to and from the balloon. The conduit may further be coupled to a pump (see, e.g., pump 920 as shown in FIG. 9), a syringe or other piston-actuated device (see, e.g., syringe 830 as shown in FIG. 8(*a*)), a pressurized reservoir (see, e.g., IV as shown in FIG. 8(*b*)), or another source of fluid (i.e., gas or liquid) to inflate the balloon. In some embodiments, the conduit may extend through the interior of the insert, such as within a cannulated portion of the insert (see, e.g., cavity 320 as shown in FIG. 3(*a*)). In other embodiments, the conduit may extend along the exterior of the insert (see generally catheters 3812, 3912 as shown in FIGS. 34-35).

In contemplated embodiments, the balloon (e.g., balloons 2120, 2130 as shown FIGS. 21-23) is in direct communication with fluid passing through the cannulated portion of the insert, such that the fluid inflates the balloon. In some such embodiments, the fenestration(s) of the insert include a pressure-actuated valve (e.g., slit valve) that remains closed until fluid pressure in the cannulated portion of the insert is sufficient to inflate the balloon. As such, the fluid first inflates the balloon and then once pressure is sufficient to open the valve, the fluid flows from the insert via the fenestration. The fenestration may further include a restrictor (e.g., narrow tube) adjacent to the valve to reduce the exit velocity of fluid flowing from the fenestration. In some embodiments, the insert includes more than one balloon configured to be inflated by the fluid passing through the cannulated portion of the insert.

In another contemplated embodiment, the balloon (e.g., balloons 2120, 2130 as shown FIGS. 21-23) includes materials configured to react chemically with one another to inflate the balloon. In some such embodiments, the operator may mix the materials to initiate the reaction by breaking a thin membrane in the balloon, removing a mechanical gate between the materials, piercing a capsule containing one of the materials, or in other ways. In some embodiments, the operator may mix the materials while the insert is positioned in an associated bone screw, or may start the reaction prior to insertion of the insert in the associated bone screw.

In yet another contemplated embodiment, the balloon (e.g., balloons 2120, 2130 as shown FIGS. 21-23) includes materials that change phase when inserted in an associated bone screw or directly into a bone. In some such embodiments, the materials are kept at a low temperature (e.g., below freezing) prior to use, and then body heat at least partially changes the phase of the materials so that the materials expand the balloon. In some such embodiments, the materials at least partially change phase from liquid to gas, or from solid to liquid. Heated or cooled fluid (e.g., saline, medicine) passed through the insert may control the degree of expansion or contraction, such as to deflate or further inflate the balloon or balloons.

In some contemplated embodiments, the balloon may be permanently inflated or inflated prior to use, and subsequently slid through the cannulated portion of the bone screw. In some such embodiments, inserting the inflated balloon into the cannulated portion of the bone screw compresses the lateral sides of the balloon against the interior surface of the bone screw, forming a movable seal as the inflated balloon is moved through the bone screw. In some embodiments, the bone screw is pre-filled with saline, which is pushed forward through fenestrations in the bone screw as the inflated balloon moves forward into the cannulated portion. In other embodiments, a catheter extending over or around the balloon allows for removal of the pre-filled saline as the inflated balloon moves forward into the cannulated portion of the bone screw (see generally catheters 3812, 3912 as shown in FIGS. 34-35).

Timing of the inflation may vary in different embodiments. Still referring to FIGS. 21-23, 30(*a*)-(*b*), and 33(*a*)-(*c*), in some embodiments, the balloon may be inflated prior to use and subsequently slid through the cannulated portion of the associated bone screw as described. In other embodiments, such as those using a conduit to fill the balloon, the balloon may be deflated when initially inserted into the bone screw, and then inflated when in proper position. To move the seal produced by such a balloon, the balloon may then be deflated again, moved, and re-inflated. In still other embodiments, the balloon may be initially deflated, moved to a position in the associated bone screw, inflated, such as by chemical reaction or a temperature-dependent phase change, and then permanently deflated following use of the bone screw to facilitate removal of the insert from the bone screw.

In alternate contemplated embodiments, the degree of flow restriction provided by the expandable portion (e.g., balloon or other expandable devices) of the insert may vary. In some embodiments, the expandable portion may fully or substantially block all communication of fluids around the expandable portion, providing a complete seal sufficient to withstand the pressures of fluids in the bone or fluids passing though the insert and bone screw. In other embodiments, the expandable portion is configured to only partially block communication of fluids around the expandable portion. In some such embodiments, the expandable portion may serve to slow the communication of fluids, such as for slow release of medications to a fenestration on the opposite side of the expandable portion in the bone screw. In still other embodiments, the degree of flow restriction may be purposely controlled by adjusting the pressure or configuration (e.g., shape, position, orientation) of the expandable portion.

Referring now to FIGS. 34-35, an insert 3310 for a fenestrated bone screw (e.g., fenestration 2170 as shown in FIG. 21; fenestrations 2918 and 2920 as shown in FIGS. 30(*a*)-(*b*)) includes one or more expandable portions 3312, 3314 configured to expand diametrically (e.g., along two axes of the three-dimensional coordinate system, in a plane, laterally) by lengthwise compression of the expandable portions 3312, 3314. As the expandable portions are compressed along the longitudinal axis of shaft 3316 of the insert 3310, the expandable portions 3312, 3314 bulge laterally and may serve as seals within the cannulated portion of an associated bone screw to isolate specific fenestrations of the bone screw for communication of medication (e.g., antibiotics). Accordingly, the insert of FIGS. 34-35 includes expandable portions 3312, 3314 configured to expand laterally (i.e., orthogonal to the shaft 3316 of the insert 3310) without requiring inflation of the expandable portions 3312, 3314.

In some embodiments, the expandable portions 3312, 3314 are at least partially formed from an elastic polymer. The expandable portions 3312, 3314 may be closed- or open-volumes, may be filled with air, liquid, gel, or may be solid, flexible structures. Additionally, the material of the expandable portions 3312, 3314 may be arranged or configured so that an end or both ends of the expandable portions 3312, 3314, as opposed to the middle, expand laterally outward.

Still referring to FIGS. 34-35, the insert includes a floating portion 3318 of the insert 3310 (i.e., moving portion, sliding portion) that slides along the shaft 3316 of the insert 3310. In some such embodiments, sliding of the floating portion 3318 allows for lengthwise compression of one or more of the expandable portions 3312, 3314, which diametrically expand laterally. In some embodiments the floating portion 3318 includes a rigid member 3320 (e.g., sleeve, cylinder, brace) adjoined on both ends by the expandable portions 3312, 3314. The rigid member 3320 of the floating portion 3318 of the insert 3310 may be cannulated and fenestrated for fluid delivery or removal.

In other embodiments, the rigid member 3320 may be permeable but not fenestrated, such as for slower time-release of medications or other fluids. In still other embodiments the rigid member 3320 of the floating portion 3318 of the insert 3310 is solid, not cannulated. In some such embodiments, the rigid member 3320 of the floating portion 3318 includes one or more solid beams or braces that separate plates 3322 to which the expandable portions 3312, 3314 are connected. The solid beams are positioned outside of the shaft 3316 of the insert 3310, and the plates 3322 are annular and slide along the shaft 3316 of the insert 3310.

According to an exemplary embodiment, the insert 3310 further includes an attachment point 3326 for a corresponding insertion tool, and possibly for fluid delivery or removal. In some embodiments, the actuation area 3324 (e.g., slide, control area) includes a coupling or connector for attachment and locking of the floating portion 3318 to the shaft 3316 to maintain compression of the expandable portions 3312, 3314. The actuation area 3324 may also be used as a point of attachment for medication or other fluid delivery or removal. In some embodiments, the plates 3322 may also be fenestrated and allow for delivery or removal of fluids. The insert 3310 further includes an end plate 3328 that is fixed to the shaft 3316, which in some embodiments anchors the floating portion 3318 of the insert 3310.

According to an exemplary embodiment, the actuation area 3324 is configured to be locked or otherwise held in a fixed position along the shaft 3316 of the insert 3310. As such, when the expandable portions 3312, 3314 are compressed and extending laterally, locking the actuation area 3324 to the shaft 3316 holds the expandable portions 3312, 3314 in the extended position. In some embodiments, the shaft 3316 is threaded and the actuation area 3324 is locked in place via a nut (e.g., jam nut). In other embodiments, the shaft 3316 is notched and the actuation area 3324 is ratcheted into position via a pawl. In still other embodiments, the shaft 3316 includes apertures or loops for pins, hooks, latches, or other fasteners. In yet other embodiments, the actuation area 3324 includes a collar that is tightened around the shaft 3316 to lock the actuation area 3324 to the shaft 3316. Other locking features may be used.

Figure 36:
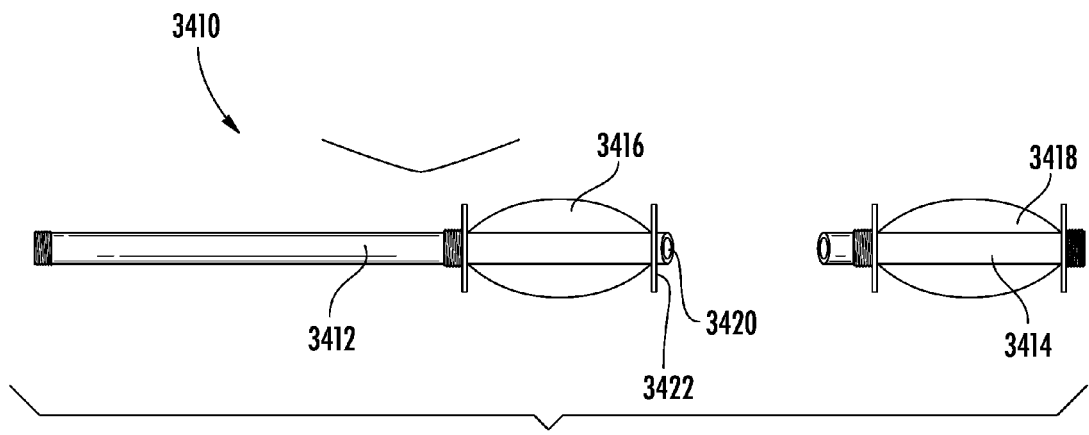
FIG. 36 is a schematic cross-sectional view of an assembly, such as an insert for the bone screw of FIG. 21, in a first configuration according to another exemplary embodiment.
Figure 37:
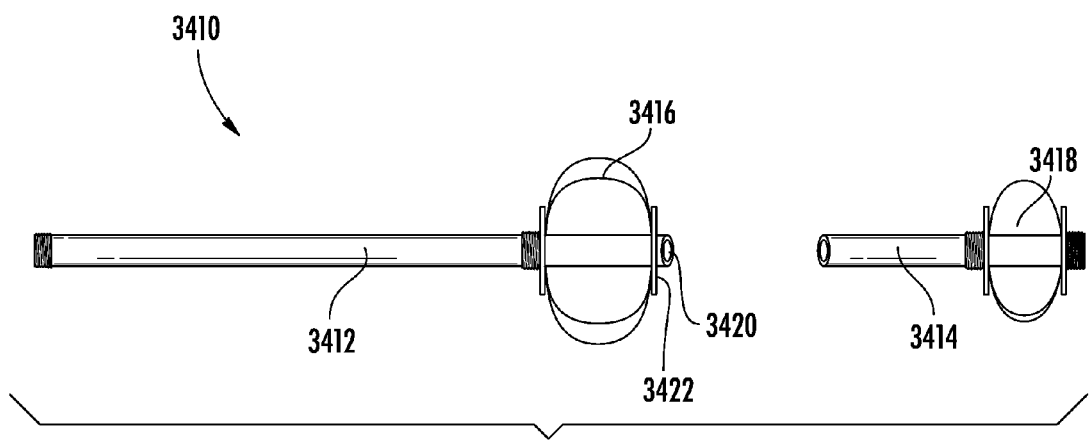
FIG. 37 is a schematic cross-sectional view of the assembly of FIG. 36 in a second configuration.

Referring now to FIGS. 36-37, an insert 3410 for a fenestrated bone screw includes two separate parts 3412, 3414. Each part 3412, 3414 includes a corresponding expandable portion 3416, 3418 configured to expand diametrically by lengthwise compression of the expandable portions 3416, 3418, allowing for isolation of specific fenestrations of the bone screw for fluid delivery or removal. In some embodiments, the forward part 3414 may be initially joined with the rearward part 3412 of the insert 3410, and then separated during insertion or expansion of the expandable portions 3416, 3418. In other embodiments, the forward part 3414 is inserted first and the expandable portion 3418 is expanded, and then the rearward portion 3412 is inserted and the expandable portion 3416 is expanded. Medications or other fluids may be communicated through openings in the end 3420 or end plate 3422 of the rearward part 3412.

Figure 38:
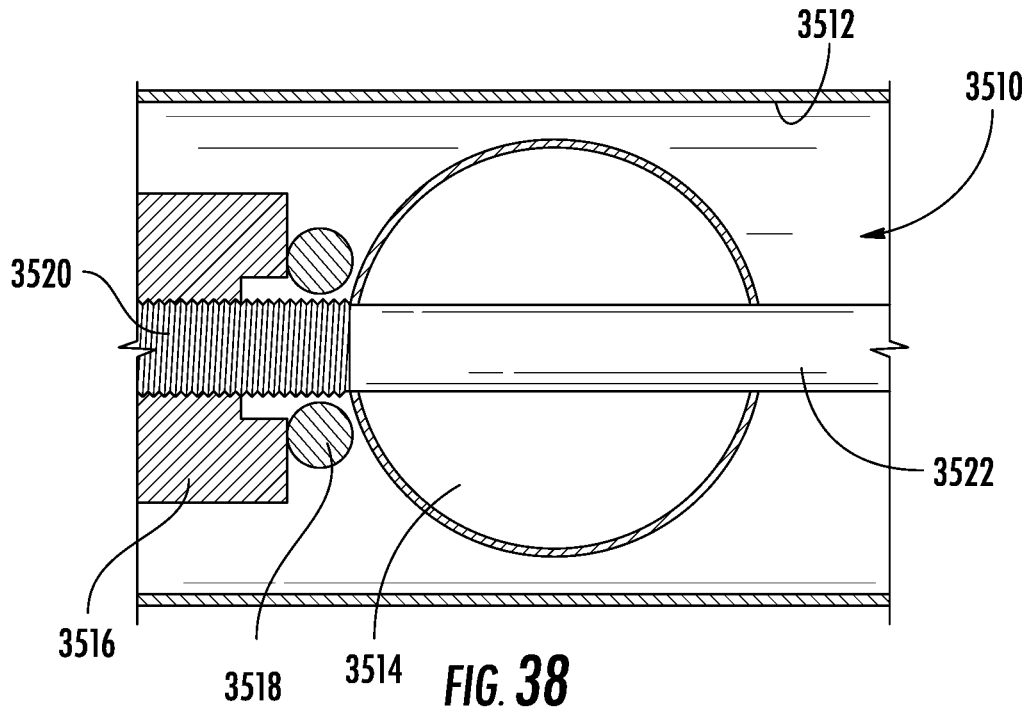
FIG. 38 is a schematic cross-sectional view of an assembly, such as an insert for the bone screw of FIG. 21, in a first configuration according to yet another exemplary embodiment.
Figure 39:
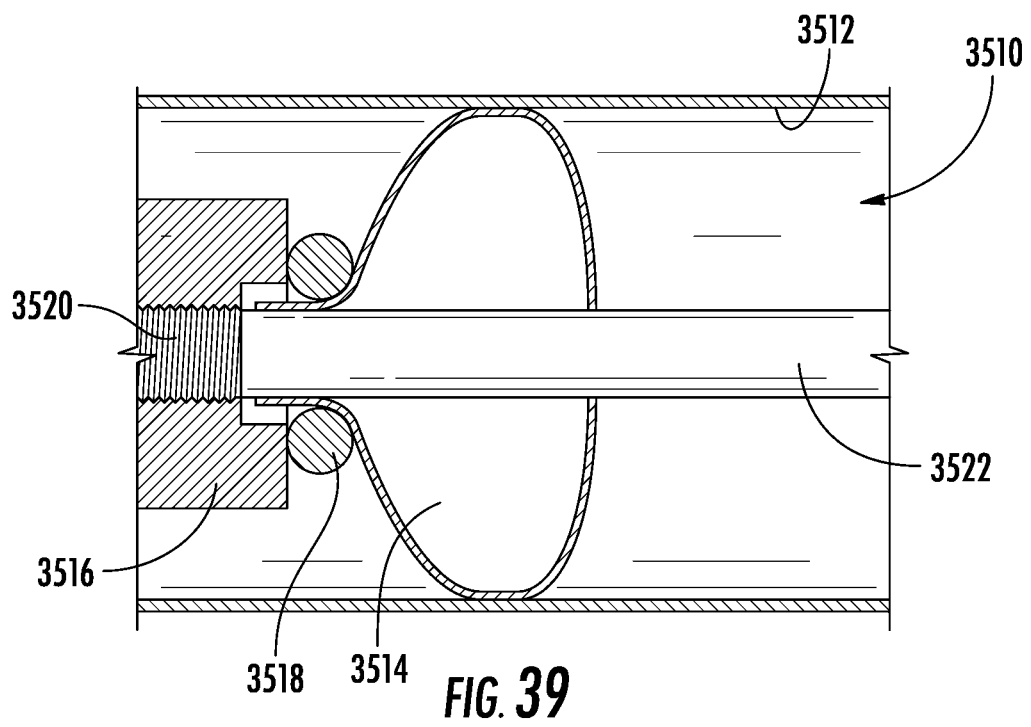
FIG. 39 is a schematic cross-sectional view of the assembly of FIG. 36 in a second configuration.

Referring to FIGS. 38-39, an insert 3510 is configured to be positioned in a cannulated portion of a bone screw 3512. The insert 3510 includes an expandable portion in the form of a fluid-filled balloon 3514. The insert 3510 further includes a sleeve 3516 and a constricting member 3518 (e.g., roller).

In a first configuration, the fluid-filled balloon 3514 has a relatively narrow lateral cross section, and is configured to freely move within the cannulated portion of the bone screw 3512. The sleeve 3516 may be moved closer to the balloon 3514, such as by engaging a threaded or ratcheted portion 3520 of the shaft 3522 of the insert 3510, pushing the constricting member 3518 over a portion of the fluid-filled balloon 3514. Squeezing the balloon 3514 causes a portion of the balloon 3514 to expand laterally outward, orthogonal to the shaft 3522. When laterally expanded, the fluid-filled balloon 3514 seals between the shaft 3522 of the insert 3510 and the bone screw 3512.

Figure 40:
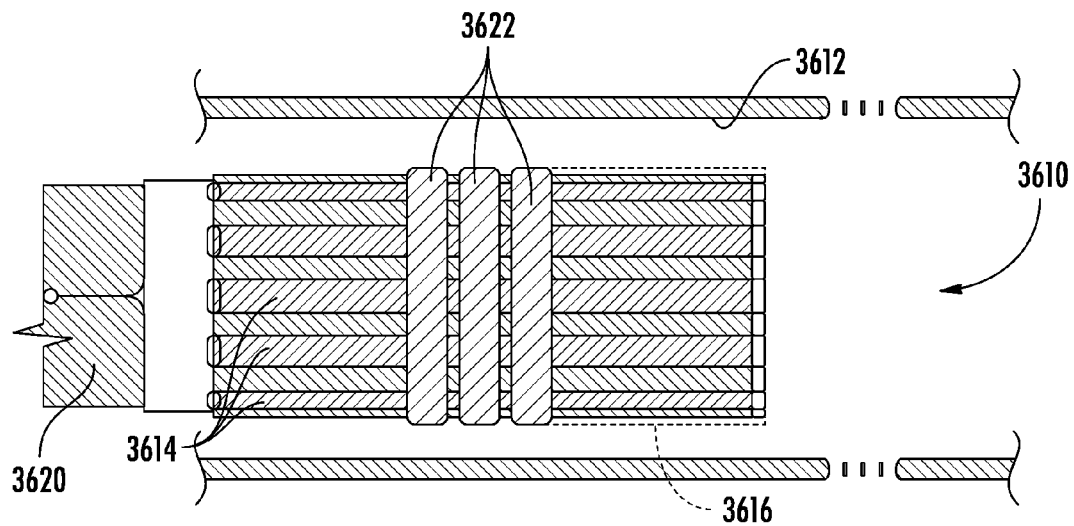
FIG. 40 is a schematic cross-sectional view of an assembly, such as an insert for the bone screw of FIG. 21, in a first configuration according to another exemplary embodiment.
Figure 41:
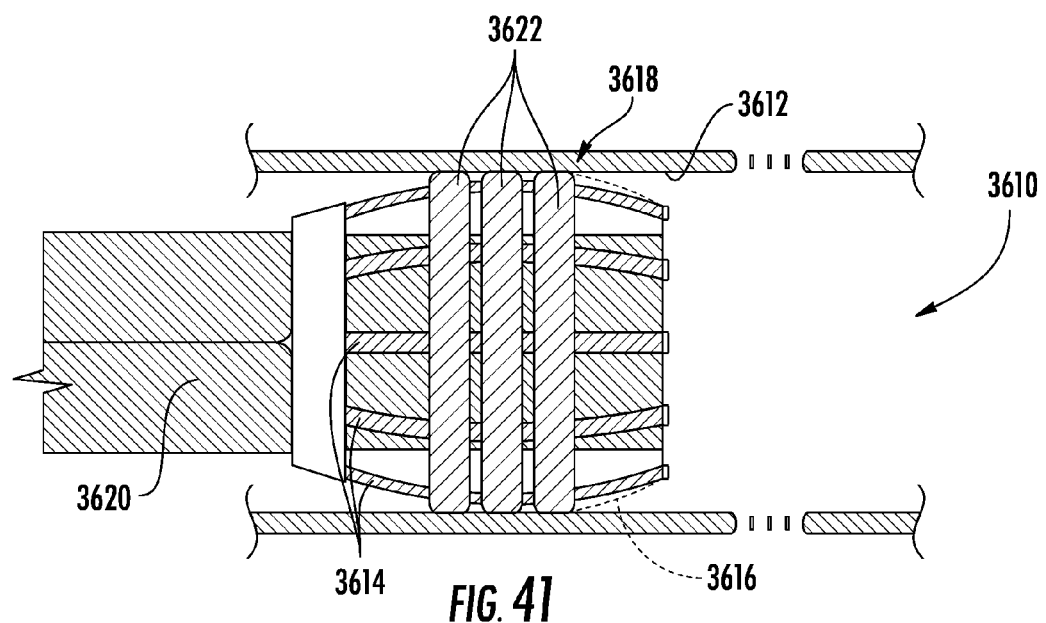
FIG. 41 is a schematic cross-sectional view of the assembly of FIG. 40 in a second configuration.

Referring to FIGS. 40-41, an insert 3610 is configured to be positioned in a cannulated portion of a bone screw 3612. The insert 3610 includes an expandable portion formed from flexible beams 3614 (e.g., flat springs) that support an impermeable cover 3616 (e.g., polymeric bladder). Lateral expansion of the flexible beams 3614 pushes the impermeable cover 3616 in contact with the cannulated portion of the bone screw 3612, forming a seal 3618 (FIG. 41). In some embodiments, the flexible beams 3614 are driven outward by compression of opposite ends of the beams 3614, much like expandable portions 3312, 3314 shown in FIGS. 34-35.

In other embodiments, the flexible beams 3614 are predisposed to bend outward, and are held flat against the shaft 3620 during placement of the insert 3610 or movement of the insert 3610 within the cannulated portion of the bone screw 3612. In contemplated embodiments, the expandable portions 3312, 3314 shown in FIGS. 34-35 are formed from flexible, rubber-like material that is likewise predisposed to expand laterally, and is tensioned to draw the expandable portions 3312, 3314 closer to the shaft 3316 of the insert 3310 during movement of the insert 3310 with respect to the cannulated portion of the bone screw.

In some embodiments, hoops 3622 or rings may extend around the flexible beams 3614 to improve the seal 3618 provided by the impermeable cover 3616 when the flexible beams 3614 are laterally expanded. The hoops 3622 may be formed from sliding rigid members, or may be a flexible, polymeric gaskets or O-rings.

In contemplated embodiments, flexible members similar to the flexible beams 3614 may be formed from metals having different thermal coefficients of expansion (e.g., bi-metallic strips). In some embodiments, heat transfer from the body may be sufficient to expand the flexible members. In other embodiments, warm or cool fluid transferred via the insert may be sufficient to control lateral expansion or contraction of the flexible members. In still other contemplated embodiments, a shape-memory alloy may be used to form the flexible members, where the alloy returns to a laterally expanded shape when heated via body heat or warm fluid transferred through the insert.

Figure 42:
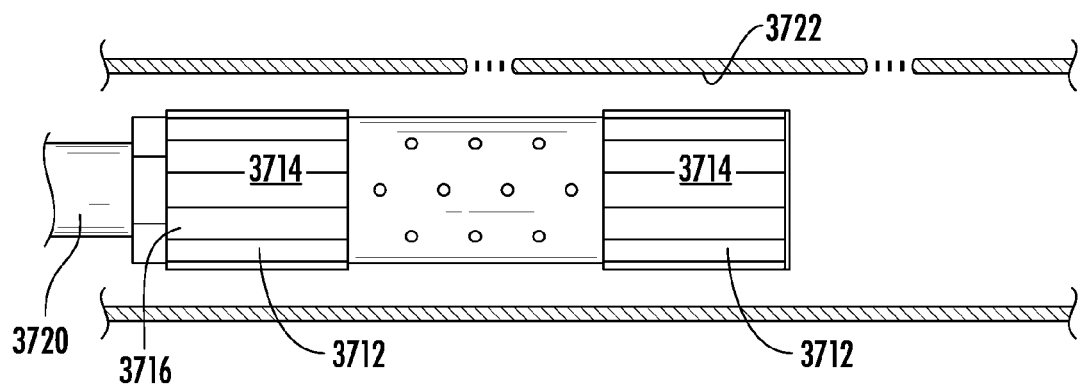
FIG. 42 is a schematic cross-sectional view of an assembly, such as an insert for the bone screw of FIG. 21, in a first configuration according to another exemplary embodiment.
Figure 43:
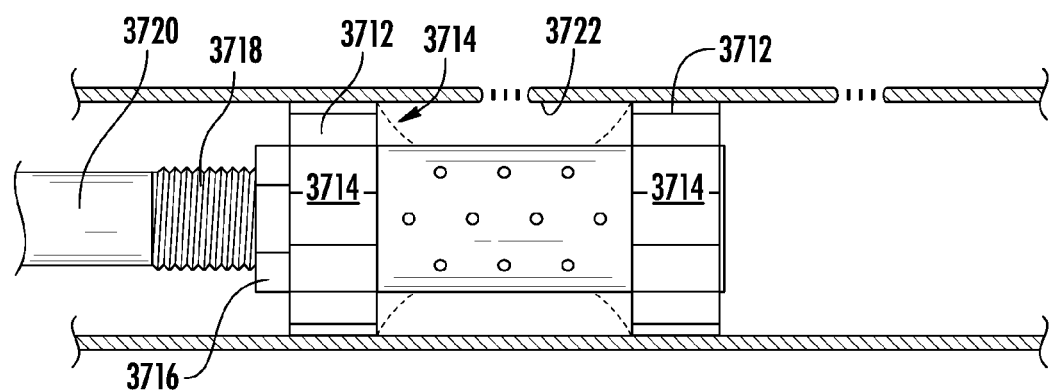
FIG. 43 is a schematic cross-sectional view of the assembly of FIG. 42 in a second configuration.

Referring to FIGS. 42-43, expandable portions of an insert 3710 include tubes of interwoven fibers 3712 (e.g., stent-like structures) that support an impermeable cover 3714. Lengthwise compression of the tube of interwoven fibers 3712 expands the impermeable cover 3714 laterally outward to form a seal. A nut 3716 may be tightened on a threaded portion 3718 of the shaft 3720 of the insert 3710 to compress the tubes of interwoven fibers 3712, causing the tubes of interwoven fibers 3712 to laterally expand and form seals between the insert 3710 and the cannulated portion of the bone screw 3722.

In still other contemplated embodiments, an umbrella-like structure is used to laterally expand an annular diaphragm to seal the cannulated portion of a bone screw. Arms of the umbrella-like structure extend from the insert to support the diaphragm. Outward movement of the arms extends the diaphragm to form a concave, annular, bowl-shaped seal between the insert and the bone screw. The well of the bowl faces the area of higher pressure so that the rim of the bowl is pressed against sides of the cannulated portion of the bone screw (e.g., flap valve).

Figure 44:
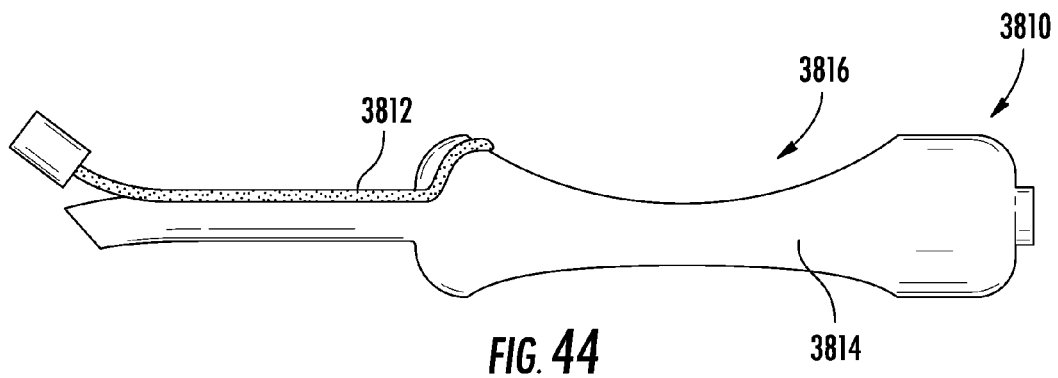
FIG. 44 is a schematic cross-sectional view of an assembly, such as an insert for the bone screw of FIG. 21, according to another exemplary embodiment.
Figure 45:
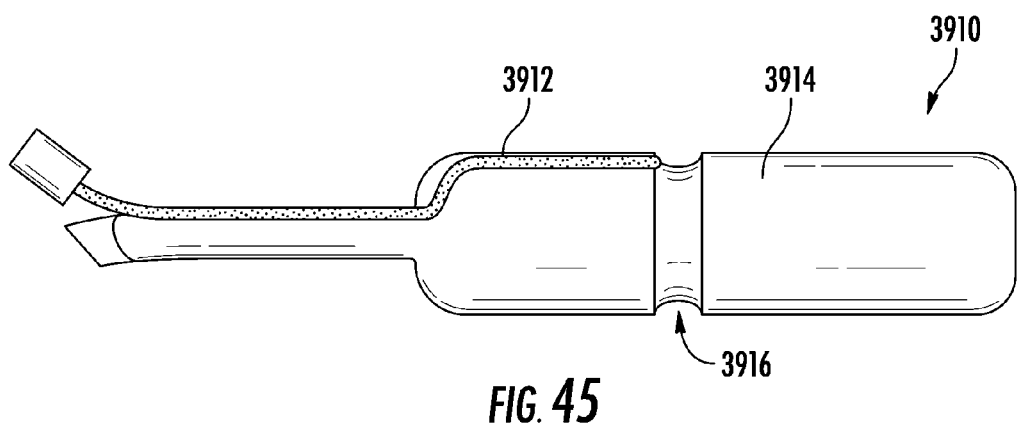
FIG. 45 is a schematic cross-sectional view of an assembly, such as an insert for the bone screw of FIG. 21, according to yet another exemplary embodiment.

Referring now to FIGS. 44-45, inserts 3810, 3910 includes catheters 3812, 3912 (e.g., conduit, passage) located on the perimeter of expandable portions 3814, 3914 of the inserts 3810, 3910. In some embodiments, the catheters 3812, 3912 are configured to communicate fluid around the expandable portions 3814, 3914 when the expandable portions 3814, 3914 are laterally expanded and forming seals in respective cannulated portions of bone screws.

In contemplated embodiments, the exterior of the catheters 3812, 3912 may be configured to deform or flex under pressure provided by the expandable portions 3814, 3914 in order to maintain seals between the interior of the respective bone screws and the expandable portions 3814, 3914 when the expandable portions 3814, 3914 are in the laterally-expanded positions.

According to an exemplary embodiment, the catheters 3812, 3912 connect to the recessed portions 3816, 3916 of the respective inserts 3810, 3910. In other embodiments, the catheters 3812, 3912 extend through the expandable portions 3814, 3914 or through cannulated passages in the inserts 3810, 3910 to reach the recessed portions 3816, 3916.

Referring specifically to FIG. 45, the insert 3810 includes the recessed portion 3816 (e.g., channel, concavity, groove), which may be formed in the expandable portion 3814 or may be adjacent thereto, such as between two expandable portions. In some embodiments, the recessed portion 3816 may be an open volume, while in other embodiments, the recessed portion 3816 may be filled with a porous material. In some embodiments, the recessed portion 3816 extends fully around the exterior of the insert 3810, allowing fluid to spread or be received circumferentially around the insert 3810. According to an exemplary embodiment, the recessed portion 3816 may be positioned adjacent to bone screw fenestrations isolated by the expandable portion 3814.

In alternative exemplary embodiments, inserts as disclosed herein may be used without a bone screw, to be directly inserted into a bone such as for purposes of irrigating the bone with antibiotics, saline, other medicines, or other fluids prior to screw placement. In some embodiments, the insert may be placed directly into a bone via guide wire placement or reaming, without a bone screw or other intermediate device between the insert and bone. The insert may include expandable portions to control the flow of fluids directly between the bone and insert. The expandable portions of such inserts may be mechanically expanded (see, e.g., FIGS. 40-43), inflated (see, e.g., balloons 2120, 2130 as shown FIGS. 21-23), or predisposed to expand and released in a controlled manner.

While in some embodiments disclosed herein the insert is cannulated and has a single passage for communication of fluids, in other embodiments the insert may include a second conduit for suction of fluids after irrigation. As such, one passage may provide fluid while the other passage concurrently removes fluid. Following irrigation, the insert may be removed and a bone screw may then be inserted into the irrigated opening in the bone. The same insert or another insert, may then be inserted into bone screw to deliver medications or other fluids. Such a process may be particularly beneficial for treating open long-bone fractures.

In some embodiments, inserts disclosed herein may be used with devices other than bone screws. In some such embodiments, inserts are positioned in nails or other fastening devices. Furthermore, various fluids may be used with the inserts and bone screws disclosed herein, including saline, antibiotics, glue, and other fluids.

Further modifications and alternative embodiments of various aspects of the invention will be apparent to those skilled in the art in view of this description. Accordingly, this description is to be construed as illustrative only. The construction and arrangements of the bone screws and inserts, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for communicating fluid to or from a bone, comprising:
    an insert comprising:
        a shaft extending between proximal and distal ends of the insert, wherein the shaft is cannulated along at least a portion of the shaft between the proximal and distal ends;
        a fenestration disposed along the cannulated portion of the shaft; and
        an expandable portion coupled to the shaft, wherein outer surfaces of the expandable portion are configured to expand laterally outward to increase the cross-sectional area of the expandable portion orthogonal to the shaft;
    a bone screw comprising:
        a shaft extending between proximal and distal ends of the bone screw, wherein the shaft is cannulated along at least a portion of the shaft, and wherein the bone screw is adapted to receive the insert in the cannulated portion of the shaft of the bone screw;
        a first fenestration located along the cannulated portion of the shaft of the bone screw; and
        a second fenestration located along the cannulated portion of the shaft of the bone screw.

2. The system of claim 1, wherein the expandable portion is a first expandable portion coupled to the shaft of the insert between the fenestration of the insert and the proximal end of the insert, and wherein the system further comprises a second expandable portion coupled to the shaft of the insert between the fenestration of the insert and the distal end of the insert.

3. The system of claim 1, wherein the first and second expandable portions of the insert are configured to expand laterally outward causing outer surfaces of the first and second expandable portions to contact an interior surface of the bone screw in the cannulated portion of the shaft of the bone screw to form seals between the insert and the bone screw.

4. The system of claim 3, wherein the insert is moveable within the cannulated portion of the shaft of the bone screw between a first position in which fluid is communicated through the first fenestration of the bone screw, and a second position in which fluid is communicated through the second fenestration of the bone screw.

5. The system of claim 4, wherein the first and second expandable portions of the insert are spaced apart such that:
    in the first position, the first fenestration of the bone screw, but not the second fenestration, is located between first and second expandable portions of the insert; and
    in the second position, the second fenestration of the bone screw, but not the first fenestration, is located between the first and second expandable portions of the insert.

6. The system of claim 1, wherein the expandable portion comprises a balloon, and wherein the balloon expands laterally outward when inflated.

7. The system of claim 1, wherein the expandable portion expands laterally outward without inflation.

8. The system of claim 7, wherein the expandable portion expands laterally outward when compressed longitudinally along the shaft of the insert.

9. The system of claim 8, wherein at least one end of the expandable portion moves with respect to the shaft of the insert when the expandable portion is compressed.

10. The system of claim 9, wherein the expandable portion is formed from an elastic polymeric material.

11. The system of claim 7, wherein the expandable portion is a first expandable portion, wherein the system further comprises a second expandable portion, and wherein the first and second expandable portions are configured to constrain fluid flow therebetween.

12. The system of claim 11, wherein first expandable portion is coupled to the shaft of the insert between the fenestration of the insert and the proximal end of the insert, and the second expandable portion is coupled to the shaft of the insert between the fenestration of the insert and the distal end of the insert, wherein the second expandable portion expands laterally outward when compressed lengthwise along with a longitudinal axis of the shaft of the insert, and wherein the first and second expandable portions are connected to one another via a rigid member.

13. The system of claim 12, wherein the rigid member is cannulated and fenestrated.

14. The system of claim 12, wherein the rigid member is cannulated and permeable.

15. The system of claim 11, wherein the shaft of the insert is a first shaft of the insert, wherein the second expandable portion is coupled to a second shaft of the insert, and wherein the second shaft of the insert is not attached to the first shaft of the insert.

16. The system of claim 15, wherein the distal end of the first shaft of the insert comprises a stopper that adjoins the first expandable portion, and wherein the fenestration of the insert is located on or adjacent to the stopper.

17. The system of claim 1, further comprising a catheter extending longitudinally over a periphery of the expandable portion.

18. The system of claim 17, wherein the expandable portion comprises or is adjacent to a recessed area to which the catheter is directed such that the catheter is configured to communicate fluid to or from the recessed area.

19. The system of claim 18, wherein the expandable portion comprises the recessed area, and further comprises a lengthwise groove within which the catheter extends and a lateral groove which forms the recessed area.

\* \* \* \* \*